United States Patent [19]
Gudas et al.

[11] Patent Number: 5,962,534
[45] Date of Patent: Oct. 5, 1999

[54] REGULATING GENE EXPRESSION USING RETINOIDS WITH CH$_2$OH OR RELATED GROUPS AT THE SIDE CHAIN TERMINAL POSITION

[75] Inventors: Lorraine J. Gudas, New York, N.Y.; Charles Achkar, North Bergen, N.J.; Jochen Buck, New York, N.Y.; Alexander W. Langston, New York, N.Y.; Fadila Derguini, New York, N.Y.; Koji Nakanishi, New York, N.Y.

[73] Assignee: Cornell Research Foundation, Inc., Ithaca, N.Y.

[21] Appl. No.: 08/887,633

[22] Filed: Jul. 3, 1997

Related U.S. Application Data

[62] Division of application No. 08/371,535, Jan. 11, 1995, Pat. No. 5,786,391.

[51] Int. Cl.$^6$ ............................ A61K 31/12; A61K 31/11
[52] U.S. Cl. ............................................ 514/690; 514/703
[58] Field of Search ..................................... 514/690, 703

[56] References Cited

U.S. PATENT DOCUMENTS

| | | | |
|---|---|---|---|
| 3,311,656 | 3/1967 | Surmatis | 560/259 |
| 3,931,257 | 1/1976 | Pawson | 554/218 |
| 4,156,100 | 5/1979 | Boguth et al. | 568/824 |
| 4,209,450 | 6/1980 | Jaedicke et al. | 554/118 |
| 4,331,814 | 5/1982 | Charbardes et al. | 560/225 |
| 4,474,983 | 10/1984 | Charbardes et al. | 560/260 |
| 5,124,083 | 6/1992 | Shealy | 514/529 |
| 5,183,817 | 2/1993 | Bazzano | 514/256 |

FOREIGN PATENT DOCUMENTS

| | | |
|---|---|---|
| 1484573 | 5/1967 | France . |
| 2305267 | 8/1973 | Germany . |

OTHER PUBLICATIONS

Sen, R., Dissertation, Columbia University, 1982, pp. 43–47.
Leo, M. A., et al, J. Biol. Chem. 260, No. 9, 5228–5231 (1985).
Surmatis, J. D., C.A. 67: 22052d (1967).
Renk, G., et al, Photochem. Photobiol. 33, 489–494 (1981).
Haag, A., et al, Helv. Chim. Acta 65, 1795–1803 (1982).
Katsuta, Y., et al, Tetrahedron Lett., 35, 905–908 (1994).
Boehm, M. F., et al, J. Am. Chem. Soc. 112, 7779–7782 (1990).
Henbest, H. B., et al, J. Chem. Soc., 4909–4912 (1957).
Williams, T. C., et al, Biochemistry 30, 2976–2988 (1991).
Haag, A., et al, Helv. Chim. Acta 63, 10–15 (1980).
Julia, M., et al, Bulletin De La Societe Chimique De France, No. 2, 746–749 (1973).
Blumberg, B., et al, Proc. Natl. Acad. Sci. USA, vol. 93, pp. 4873–4878 (May 1996).
Achkar, C. C., et al, Proc. Natl. Acad. Sci. USA vol. 93, pp. 4879–4884 (May 1996).

*Primary Examiner*—Jerome D. Goldberg

[57] ABSTRACT

For the first time, certain retinoids with a side chain terminal CH$_2$OH group or ester or ether thereof or aldehyde rather than a side chain terminal COOH group and substitution at the 4-position have been indicated to bind to nuclear receptors and to be biologically active in inducing cell differentiation of normal and tumor cells. These compounds activate gene expression through binding to nuclear receptor proteins. These compounds induce differentiation in normal and cancer cells and are useful for treating leukemias, and lymphomas, squamous cell carcinomas, deep (cystic) acne, psoriasis and photodamaged or aging skin. These compounds have stability and in vitro half-life advantages over and solubility differences from all-trans-retinoic acid and activity advantages over 13-cis retinoic acid.

5 Claims, 9 Drawing Sheets

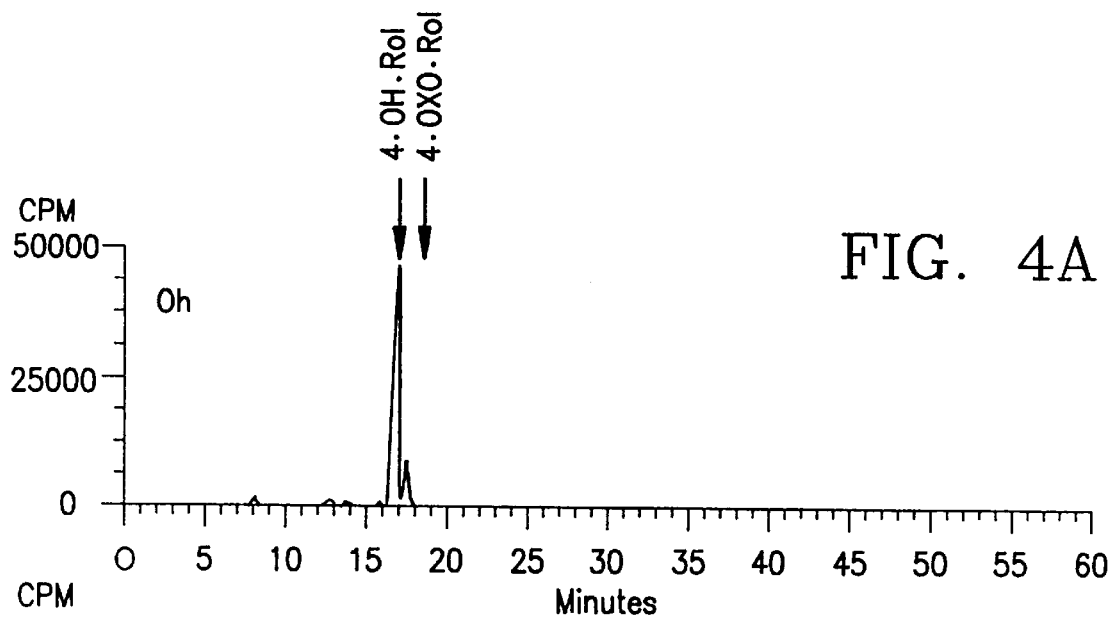
FIG. 4A
FIG. 4B
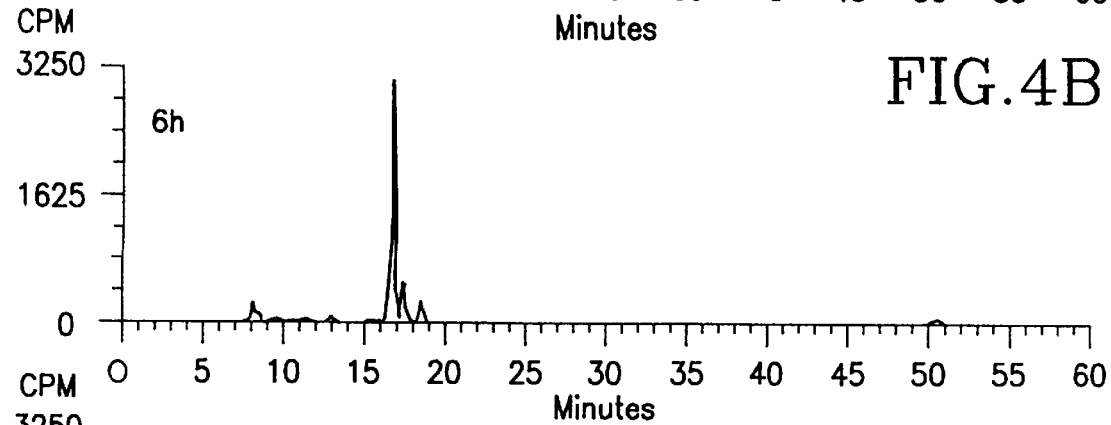
FIG. 4C
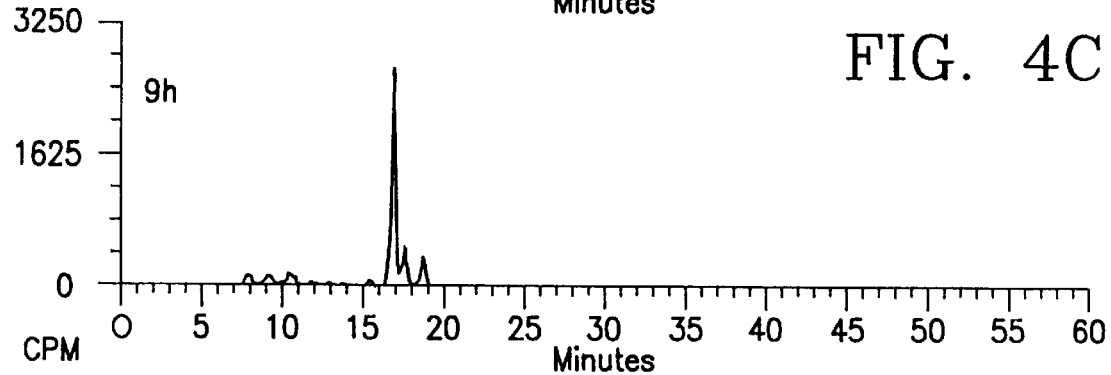
FIG. 4D
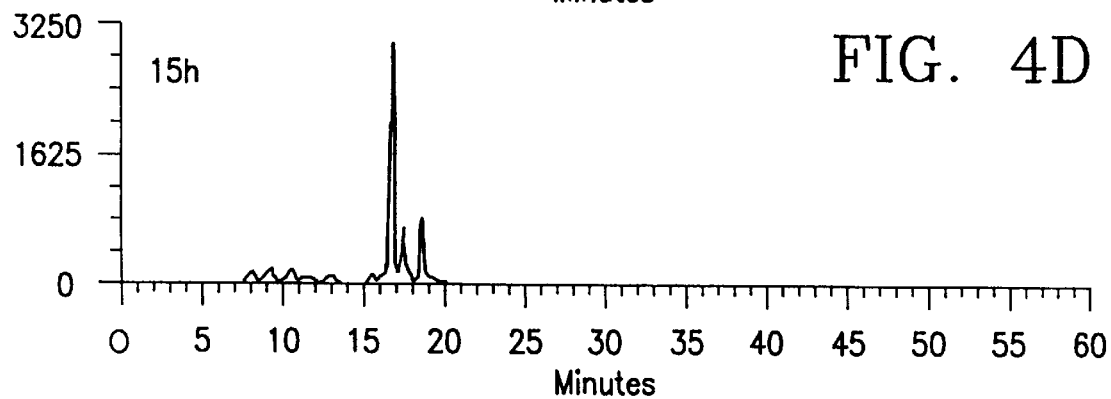

REGULATING GENE EXPRESSION USING RETINOIDS WITH CH₂OH OR RELATED GROUPS AT THE SIDE CHAIN TERMINAL POSITION

This is a divisional of application Ser. No. 08/371,535 filed on Jan. 11, 1995, now U.S. Pat. No. 5,786,391.

The invention described herein was made in the course of work under grant number R01 CA43796 from the National Institutes of Health, in the United States Government. The United States Government has certain rights in this invention.

TECHNICAL FIELD

This invention is directed to methods involving use of retinoids with CH₂OH at the side chain terminal position.

BACKGROUND OF THE INVENTION

Throughout this application various publications are referenced by arabic numerals within parentheses. Full bibliographic citations for these references may be found at the end of the specification immediately preceding the claims. The disclosures for the publications in their entireties are hereby incorporated by reference into this application to describe more thoroughly the state of the art to which this invention pertains.

The term "retinoid" has been used to define a group of compounds consisting of retinol (Vitamin A) and both natural and synthetic derivatives thereof. See Sporn, M. B., et al (1). Various metabolic derivatives of retinol have been identified. Of these, retinoic acid has been found to be crucial for normal pattern formation during embryogenesis and in the regulation of the differentiation of a variety of cell types, retinal has been found to be essential for vision, 14-hydroxy-4,14-retro-retinol has been found to have a function in the stimulation of lymphocyte growth, and anhydroretinol has been found to be an antagonist to 14-hydroxy-4,14-retro-retinol. See Gudas, L. J. (2). Other metabolic derivatives of retinol have been dismissed as biologically inactive. See Leo, M. A. et al (3). Two that have been heretofore identified but dismissed as inactive are 4-oxo-retinol and 4-hydroxyretinol.

Retinoic acid (i.e., all-trans-retinoic acid) has been orally administered in clinical trials for the treatment of acute promyelocytic leukemia. See Warrell, R. P. et al, 1991 (4) and Warrell, R. P. et al, 1993 (5). This treatment causes cell differentiation and remission for 3 or 4 months. However, this treatment induces the production of an enzyme which breaks down the retinoic acid and with continued retinoic acid dosages, this induction of enzyme production progressively increases so that the half-life of the retinoic acid becomes progressively shorter; thus the level of retinoic acid reaching the blood progressively decreases and the treatment over time becomes ineffective. See Lefebvre, P. P., et al (6); Muindi, J. R., et al (7); and Brazzel, R. K., et al (8). Other types of leukemia and lymphoma cells from patients respond to all-trans-retinoic acid by differentiating in a cell culture system. See Hong, W. K., et al (9). This indicates that other types of leukemia and lymphoma patients would benefit from retinoid therapy but all-trans-retinoic acid cannot be efficacious in such patients because of its short half-life. Many other types of carcinomas are treated with retinoic acid. See Hong, W. K., et al (9).

All-trans-retinoic acid (also known as tretinoin, Retin-A®) is also used for treatment of deep (cystic) acne, psoriasis, and other dermatological conditions but the short half-life and side effects of this compound are problems. See Peck, G. L, et al (12). All-trans-retinoic acid is also used for the treatment of liver spots. See Rafai, E. S., et al (13). All-trans-retinoic acid is also used for the treatment of wrinkling which results from photodamage and aging of the skin. See Peck, G. L., et al (12).

The 13-cis-isomer of retinoic acid (also known as isotretinoin, Accutane®) is used for treatment of deep (cystic) acne, psoriasis, and other dermatological conditions. The 13-cis isomer of retinoic acid has also been found to cause differentiation of epithelial cells, and is used to treat squamous cell carcinoma of the head and neck. See Hong, W. K., et al (9). It is speculated that it isomerizes and is progressively released as all-trans-retinoic acid, thereby lengthening the effective treatment period for this disease compared to where all-trans-retinoic acid is used per se. The 13-cis isomer of retinoic acid has also proven to be useful in the treatment of squamous cell carcinoma of the cervix and of the skin, when used in combination with α-interferon. See Lippman, S. M., et al (10) and Lippman, S. M., et al (11).

Carcinoma of the breast is treated with 4-hydroxyphenylretinamide, a synthetic retinoid. See Hong, W. K., et al (9).

SUMMARY OF THE INVENTION

It has been discovered herein that 4-oxo-retinol is biologically active and can be successfully used for the treatments where all-trans-retinoic acid and 13-cis retinoic acid have been used but with the advantages over all-trans-retinoic acid that it has different biological properties (e.g., is more water soluble) and that it does not induce production of enzyme which degrades it to inactive form; and that it has a much longer half-life than all-trans-retinoic acid; and with the advantage over 13-cis retinoic acid that it is active per se; and consequently is more effective than all-trans-retinoic acid and 13-cis retinoic acid.

It has further been discovered that while all-trans-retinoic acid binds equally well to α-, β-, and γ-retinoic acid receptors which mediate the activity thereof as is described in Mangelsdorf, D. J., et al (14), 4-oxo-retinol binds well to α- and β-retinoic acid receptors for the mediation of its activity but binds less well to the γ-retinoic acid receptor for the mediation of its activity. Since various cells do not contain all of these receptors or contain different levels of these receptors, 4-oxo-retinol has the additional advantage over all-trans-retinoic acid that its actions are more localized and more specific.

It has further been discovered that 4-hydroxyretinol is metabolically converted to 4-oxo-retinol in cells indicating that it is a precursor of 4-oxo-retinol in vivo.

These discoveries are the basis for the following embodiments of the invention herein.

In these embodiments, the retinoids are binding effective retinoids with CH₂OH (the alcohol form) or ester thereof (the ester form) or ether thereof (the ether form) or CHO (the aldehyde form) at the side chain terminal position and in the alcohol form preferably have the structure

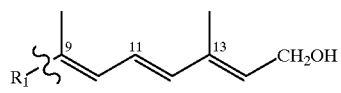

wherein the configuration at the 7-, 9-, 11- and 13-position double bonds is independently Z or E and wherein R₁ is selected from the group consisting of

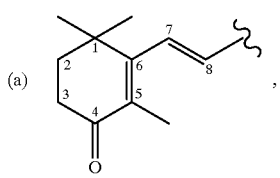 (I)

(a)

wherein the keto group at the 4-position is free or protected, or is replaced by a thioketone group which is free or protected or is replaced by $C_{1-6}$-alkylidene group;

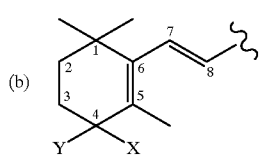 (II)

(b)

wherein X is selected from the group consisting of hydrogen and $C_{1-6}$-alkyl and wherein Y is selected from the group consisting of $C_{1-6}$-alkyl, hydroxyl, alkoxyl, acyloxyl, halide, azide, sulfhydryl, amine and $C_{1-6}$-alkyl substituted amino and wherein the absolute configuration at the 4-position is independently R or S;

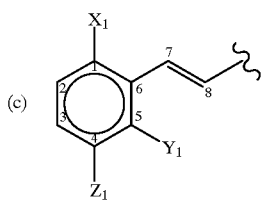 (III)

(c)

wherein $X_1$, $Y_1$ and $Z_1$ are independently selected from the group consisting of hydrogen, $C_{1-6}$-alkyl, hydroxyl, alkoxyl, acyloxyl, halide, azide, sulfhydryl, amine and $C_{16}$-alkyl substituted amino;

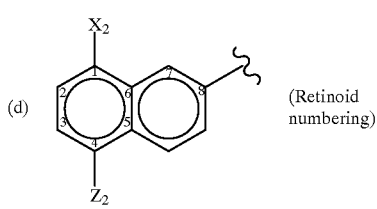 (IV)

(d) (Retinoid numbering)

wherein $X_2$ and $Z_2$ are independently selected from the group consisting of hydrogen, $C_{1-6}$-alkyl, hydroxyl, alkoxyl, acyloxyl, halide, azide, sulfhydryl, amine and $C_{1-6}$-alkyl substituted amino;

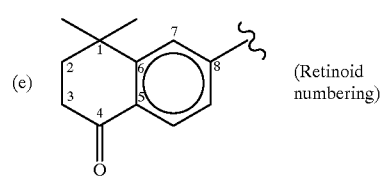 (V)

(e) (Retinoid numbering)

wherein the keto group at the 4-position is free or protected or is replaced by a thioketone group which is free or protected or is replaced by $C_{1-6}$-alkylidene group; and

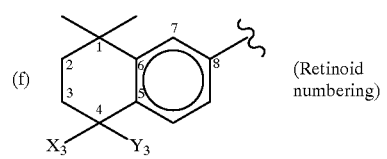 (VI)

(f) (Retinoid numbering)

wherein $X_3$ and $Y_3$ are independently selected from the group consisting of hydrogen, $C_{1-6}$-alkyl, hydroxyl, alkoxyl, acyloxyl, halide, azide, sulfhydryl, amine and $C_{1-6}$-alkyl substituted amino.

The ester form contains ester group which is converted to alcohol in the body once administered or provides active compound without such conversion and said ester group normally contains from 1 to 16 carbon atoms if saturated, e.g., acetate or palmitate, or up to 20 carbon atoms if unsaturated, or is a modified sugar, e.g., a glucuronide.

The ether form is the $C_{1-6}$-alkyl ether.

These retinoids will be referred to hereinafter as the retinoids herein. The term "the retinoids herein" is limited to such retinoids which originate from pharmaceutically pure compounds of the same structure and thus excludes the inherent formation of these compounds as metabolic products in the body. The term "originating from" is used herein to mean that the pharmaceutically pure compound is administered per se or after formulation and the term "pharmaceutically pure" is used herein to mean more than 95% pure and containing no unacceptably harmful impurities.

The primary alcohol, ester, ether or aldehyde moiety at the side chain terminal position together with substitution in the 4-position are general features of the retinoids herein, as distinguished from retinoids with an acid group at the 15-position.

In a first embodiment of the invention herein, there is provided a method of inducing differentiation of normal and cancer cells, in vitro and in vivo, comprising contacting the cells with a differentiation-inducing effective amount of a retinoid herein.

In a second embodiment of the invention, there is provided a method for binding of retinoid to nuclear receptor protein including retinoic acid receptors (RARs) and retinoid X receptors (RXRs) which comprises contacting said protein with a binding effective amount of retinoid herein.

In a third embodiment of the invention, there is provided a method of regulating gene expression through binding to nuclear receptor proteins which comprises contacting a cell with a gene expression regulating effective amount of retinoid herein.

In a fourth embodiment of the invention, there is provided a method for enhancing transcription of a gene regulated by retinoids in any cell which comprises contacting the cell with a transcription enhancing effective amount of retinoid herein.

In another embodiment of the invention herein, there is provided a method for treating various types of leukemias and lymphomas including acute promyelocytic leukemia in vitro (in cell culture) or in patients afflicted with these conditions comprising administering a leukemia cell or lymphoma cell differentiation-inducing effective amount of retinoid herein.

In still a further embodiment of the invention herein, there is provided a method for treating squamous cell carcinoma including squamous cell carcinoma of the head and neck and squamous cell carcinoma of the breast, in vitro (in cell culture) or in patients afflicted with these conditions, comprising administering a squamous cell carcinoma cell differentiation-inducing effective amount of retinoid herein.

In still a further embodiment of the invention herein, there is provided a method for treating deep (cystic) acne in a patient afflicted with this condition comprising administering to said patient an acne clearing effective amount of retinoid herein.

In still a further embodiment of the invention herein, there is provided a method for treating psoriasis in a patient afflicted with this condition comprising administering to said patient a psoriasis clearing amount of retinoid herein.

In still a further embodiment of the invention herein, there is provided a method for treating photodamaged or aged skin with wrinkles in a patient afflicted with this condition comprising administering to said patient a wrinkling removing effective amount of retinoid herein.

The term "binding effective retinoid" is used herein to mean retinoid which binds to a nuclear receptor protein including one or more retinoic acid receptors and excludes retinol.

The term "differentiation-inducing effective amount" is used herein to mean an amount which results in some cancer cells changing to non-cancerous form or in which normal cells change to an overtly specialized cell type.

The term "binding effective amount" is used herein to mean sufficient compound bound to nuclear receptor protein to be measurable in binding assays.

The term "gene expression effective regulating amount" is used herein to mean an amount effective to change the amount of messenger RNA in cells.

The term "enhancing transcription of a gene" is used herein to mean the accelerated production of messenger RNA in cells. Hox a-1 and laminin B1 are two examples of genes which are regulated by retinoic acid and therefore, whose transcription may be enhanced by the use of the claimed method.

The term "contacting" is used herein to mean contacting in vitro or in vivo. Methods of in vitro and in vivo contacting are described hereinafter.

The term "transcription enhancing effective amount" is used herein to mean the amount which enhances transcription of certain genes in the cell and will vary with the type of cell as well as the gene to be regulated.

The term "acne clearing effective amount" is used herein to mean an amount which results in disappearance of the acne in an area which is at least 10% of that initially affected.

The term "psoriasis clearing effective amount" is used herein to mean an amount which results in disappearance of the psoriasis in an area which is at least 10% of that initially affected.

The term "wrinkling removing effecting amount" is used herein to mean at least a 10% reduction in wrinkling, preferably at least a 25% reduction in wrinkling, or in the reduction of epidermal pigmentation in liver spots.

Methods of determining effective amounts are well known to those skilled in the art.

The preferred retinoids herein are 4-oxo-retinol which has the structure set forth above wherein $R_1$ is (I) and 4-hydroxyretinol which has the structure set forth above where $R_1$ is (II) and X is OH and Y is H, and the corresponding esters and aldehydes as defined above.

The terms 4-oxo-retinol and 4-hydroxyretinol are used herein to mean the all-trans forms as well as isomeric forms of these including the 7-cis, 9-cis, 11-cis and 13-cis isomers, and the term 4-hydroxyretinol is used herein to mean the (4R) or (4S) enantiomeric forms.

BRIEF DESCRIPTION OF THE DRAWINGS

In FIG. 1, the parameter for the X-axis is time in minutes and the parameter for the Y-axis is counts per minute of tritium.

FIGS. 4A–4D depict HPLC analysis after incubation of F9 stem cells in the presence of 50 nM $^3$H-4-hydroxyretinol after periods of time as indicated and extraction. In FIGS. 4A–4D, "4-OH-ROl" stands for all-trans-4-hydroxyretinol, "4-OXO-ROl" stands for all-trans-4-oxo-retinol, and "CPM" stands for counts per minute of tritium. FIGS. 4A–4D sets forth results of Example V.

FIG. 5 depicts HPLC analysis after incubation of F9 stem cells in the presence of 50 nM $^3$H-4-oxo-retinol after periods of time as indicated and extraction using the method of McClean, S. W., et al. (15). FIGS. 5A–5D set forth results of Example V.

DETAILED DESCRIPTION

Figure 1A:
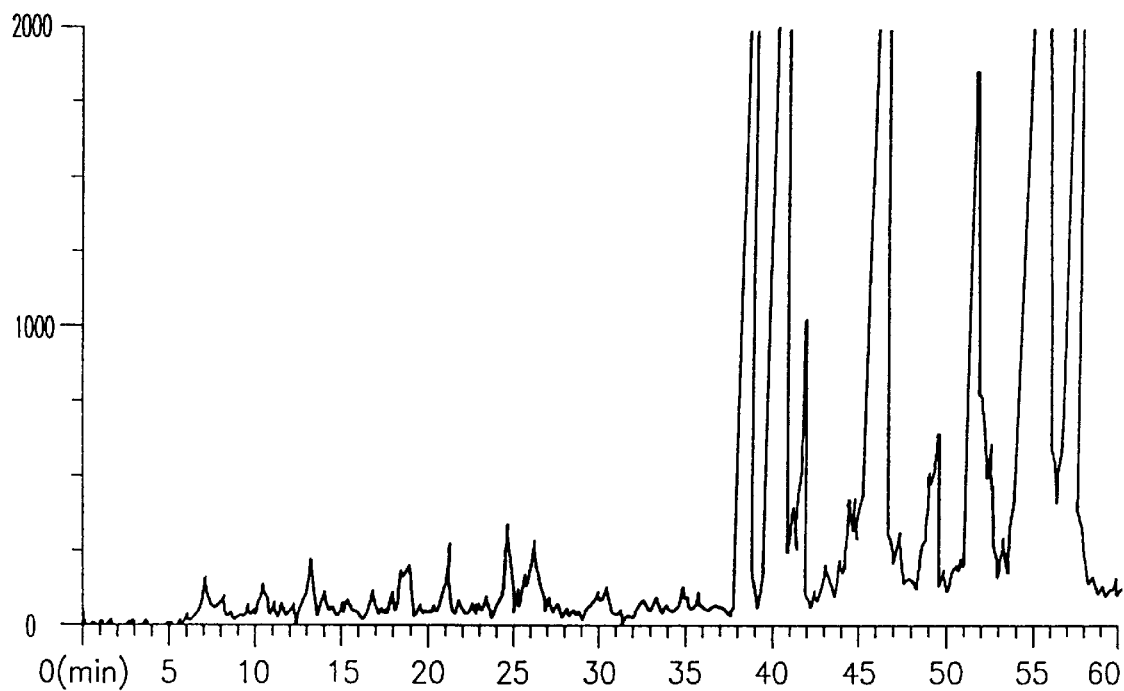
FIGS. 1(a) and 1(b) depicts HPLC radiochromatograms of F9 stem cell extracts and retinoic acid induced stem cell extracts constituting results of Example I.

We turn now to the retinoids herein. Those taught in conjunction with the above structural formula wherein $R_1$ has the structure (I) include 4-oxo-retinol and the other retinol analogs with the mentioned modifications, e.g., 4-methylidene-retinol, and the corresponding esters, ethers and aldehydes. Those taught in conjunction with the above structural formula wherein $R_1$ has the structure (II) include 4-hydroxyretinol and the other retinol analogs bearing at the 4-position the mentioned substituents, e.g., 4-dimethylamino-retinol, and the corresponding esters, ethers and aldehydes. Those taught in conjunction with the above structural formula wherein $R_1$ has the structure (III) include the phenyl analogs of retinol bearing at the indicated positions the mentioned substituents, e.g., (1-methyl-4-iodophenyl)-retinol, and the corresponding esters, ethers and aldehydes. Those taught in conjunction with the above structural formula wherein $R_1$ has the structure (IV) include the naphthyl analogs of retinol bearing at the indicated positions the mentioned substituents, e.g., (1-methyl-4-methoxy-naphthyl)-retinol and the corresponding esters, ethers and aldehydes. Those taught in conjunction with the above structural formula wherein $R_1$ has the structure (V) and wherein $R_1$ has the structure (VI) include the tetrahydronaphthyl analogs of retinol bearing at the indicated positions the mentioned substituents, e.g., (1,1-dimethyl-4-oxo-1,2,3,4-tetrahydronaphthyl)-retinol and (1,1-dimethyl-4-hydroxy-1,2,3,4-tetrahydronaphthyl)-retinol, and the corresponding esters, ethers and aldehydes.

Pharmaceutically pure 4-oxo-retinol and 4-hydroxyretinol are readily obtained by inducing differentiation in F9 mouse teratocarcinoma stem cells, an established widely used line, from a murine tumor, available from the American Type Culture Collection under accession no. ATCC CRL 1720, with retinoic acid, whereby the endogenous retinol (vitamin A) is metabolized into many derivatives in the differentiated cells, including 4-oxo-retinol and 4-hydroxyretinol, and isolating 4-oxo-retinol and 4-hydroxyretinol in pharmaceutically pure form. This can be carried out by culturing the F9 stem cells in the presence of retinoic acid (to induce differentiation) and retinol (to replace endogenous retinol as it is converted into derivatives) and extracting using the procedure of McClean, S. W., et al (15) and isolating pharmaceutically pure 4-oxo-retinol and 4-hydroxyretinol from the extract using HPLC.

The compound 4-oxo-retinol can be prepared according to several known procedures as follows: A first method involves selective $NaBH_4$ reduction of 4-oxo-retinal, obtained by $MnO_2$ oxidation of 4-hydroxy-retinal. See Boehm, M. F., et al (16). The latter can be prepared from commercially available all-trans-retinal. See Henbest, H. B., et al (17); Reedy, A. J., (18); Surmatis, J. D. (19); and Renk, G., et al (20). A second method involves the synthesis of 4-oxo-retinal by direct oxidation of retinol or retinal by $MnO_2$. See Henbest, H. B., et al (17) and Williams, T. C., et al (21). A third method involves hydrolysis of 4-oxo-retinyl acetate prepared from commercially available retinyl acetate. See Henbest, H. B., et al (17).

All-trans(4S)-4-hydroxy-retinol can be prepared starting with (4S)-4-hydroxy-β-ionone obtained as described in Haag, A., et al (22). Elongation of the side chain is achieved by conventional Horner-Emmons reactions as described in Haag, A., et al (23) and Katsuta, Y., et al (24) followed by HPLC purification.

All-trans(4R)-4-hydroxy-retinol can be obtained similarly, starting with (4R)-4-hydroxy-β-ionone obtained as described in Haag, A., et al (22).

Racemic all-trans-4-hydroxy-retinol can be synthesized by $NaBH_4$ reduction of 4-hydroxy-, or 4-oxo-retinal obtained as described in Henbest, H. B., et al (17); Reedy, A. J., et al (18); Surmatis, J. D. (19); Renk, G., et al (20); and Williams, T. C., et al (21).

Others of the retinoids herein are prepared following retinoid synthetic procedures well known to those skilled in the art. See for example Dawson, M. I., et al (39) which is incorporated herein by reference.

The methods herein for inducing differentiation in a normal cell or a cancer cell and for binding to nuclear receptor proteins and for regulating gene expression and for enhancing transcription of a gene regulated by retinoids in a cell and for treating leukemias and lymphomas and for treating squamous cell carcinoma are intended for application in vitro and in vivo. The other methods herein are intended for application in vivo.

The in vitro methods herein are readily carried out in cell culture by methods well known to those skilled in the art.

For in vivo treatment, the treatments are intended for the treatment of animals, e.g., mammals, including human patients.

For in vivo administration, administration is carried out by methods well known to those skilled in the art and include, but are not limited to, administration orally, parenterally including intravenously, and topically, and administration may be effected continuously or intermittently such that the amount of the composition in the patient is effective to obtain benefit.

The retinoids herein are readily administered in vivo as compositions comprising active compound in a pharmaceutically acceptable carrier. As used herein, the term "pharmaceutically acceptable carrier" encompasses any of the standard pharmaceutical carriers, including phosphate buffered saline solution, water, and emulsions such as an oil/water emulsion, and various types of wetting agents. In the preferred embodiment of the invention, the pharmaceutically acceptable carrier also comprises specific binding proteins, which may be, but are not limited to albumin, retinol binding proteins (RBP), transthyretin (TTR), and the complex formed by RBP and TTR.

The retinoids herein can be readily formulated with carrier for in vivo administration. Compositions for oral administration may be, for example, in capsule or pill form and comprise a therapeutically effective amount of retinoid herein and pharmaceutically acceptable excipient, e.g., inert diluent such as calcium carbonate, sodium carbonate, lactose or talc. Compositions for topical administration of retinoids herein may be, for example, in lotion, cream, ointment or gel form and comprise a therapeutically effective amount of retinoid herein and pharmaceutically acceptable carrier, e.g., propylene glycol, mineral oil, petrolatum, glyceryl monostearate and the like. Compositions for parenteral administration of retinoids herein include a therapeutically effective amount of retinoid herein and pharmaceutically acceptable carrier such as sterile water or physiological saline, and liposome delivery systems can be used to accommodate for lack of solubility.

In general, dosages for in vivo administration are 5 to 5000 mg of retinoid herein per square meter of the body per day (0.1–100 mg/kg body weight/day), preferably 50 to 200 mg of retinoid herein per square meter of the body per day, for oral administration; 5 to 5000 mg of retinoid herein per square meter of the body per day, preferably 20 to 200 mg of retinoid herein per square meter of the body per day, for parenteral administration; and 1 mg to 500 mg of retinoid herein per square inch per day, preferably from 2 mg to 50 mg of retinoid herein per square inch per day, for topical administration.

When the methods for inducing differentiation in a normal or a cancer cell and for binding to nuclear receptor protein and for regulating gene expression through binding to nuclear receptor proteins and for enhancing transcription of a gene regulated by retinoids and for treating leukemia and lymphomas and for treating squamous cell carcinoma are carried out in vitro, the contacting may be effected by incubating cells with a retinoid herein. The concentrations of the said retinoid are the concentrations which are respectively effective to cause differentiation and growth inhibition of the cell and binding to nuclear receptor protein in the cell and gene expression regulation in the cell and transcription enhancing effect in the cell and cell differentiation in lymphoma and leukemia and squamous cell carcinoma cells. The effective amount varies with the type of cell. Another factor in determining the effective amount of the compound is the degree of vitamin A deficiency in the environment. Thus, the effective concentration of retinoid herein varies with the level of vitamin A within the cell. Typical effective concentrations of 4-oxo-retinol and 4-hydroxyretinol can range from $1 \times 10^{-9}$ M to $1 \times 10^{-6}$ M.

We turn now to the embodiment of the invention directed to inducing differentiation in a normal or a cancer cell comprising contacting the cancer cell with a differentiation-inducing effective amount of retinoid herein. Example IV hereinafter shows this occurring in vitro.

We turn now to the embodiment of the invention herein directed to the method of binding to nuclear receptor proteins which comprises contacting said protein with a binding effective amount of retinoid herein. Example II shows this occurring in vitro.

We turn now to the embodiment of the invention herein directed to regulating gene expression through binding to nuclear receptor proteins which comprises contacting a cell with a gene expression regulating effective amount of retinoid herein and the embodiment of the invention of enhancing transcription of a gene regulated by retinoids in any cell which comprises contacting the cell with a transcription enhancing amount of retinoid herein. Example III shows these methods occurring in vitro.

We turn now to the embodiment of the invention directed to treating acute promyelocytic leukemia or other types of leukemias or lymphomas in patients afflicted with these conditions. This comprises administering to said patients a cell differentiation-inducing effective amount of retinoid herein. Effective dosage is readily determined by starting with a low dosage and increasing dosage until blood chemistries indicate effectiveness. Administration is continued for as many days as necessary to obtain and preserve remission. Oral administration is preferred although parenteral routes of administration are possible. Other types of leukemias and lymphomas to which the method is applicable besides acute promyelocytic leukemia include, for example, cutaneous T-cell lymphoma/mycosis fungoides which is described in Kessler, J. F., et al (25) and myelodysplastic syndrome which is described in Clark, R., et al (26).

We turn now to the embodiment of the invention directed to treating squamous cell carcinoma in a patient afflicted with this condition comprising administering to said patient a squamous cell carcinoma differentiation-inducing effective amount of retinoid herein. Effective dosage is readily determined by starting with a low dosage and increasing dosage until histological examination indicates the occurrence of cell differentiation and concomitant reduction in cell growth. Oral administration is preferred although parenteral routes of administration are possible. Administration is continued until the squamous cell carcinoma is no longer evident. This embodiment has already been described in conjunction with squamous cell carcinoma of the head and neck and carcinoma of the breast. This embodiment is also useful for treatment of the following squamous cell carcinomas: skin, cervix, colon, and lung.

We turn now to the embodiment of the invention directed to treating deep (cystic) acne in a patient afflicted with this condition comprising administering to said patient an acne clearing effective amount of retinoid herein. Preferably, administration is carried out systemically, very preferably orally and less preferably parenterally. Topical administration is also possible. Administration is continued as long as benefit is obtained.

We turn now to the embodiment of the invention directed to treating psoriasis in a patient afflicted with this condition comprising administrating to said patient a psoriasis clearing effective amount of retinoid herein. Preferably, administration is carried out systemically, very preferably orally and less preferably parenterally. Topical administration is also possible. Administration is continued as long as benefit is obtained.

We turn now to the embodiment of the invention directed to treating photodamaged or aging skin in a patient afflicted with this condition comprising administrating to said patient a wrinkling removing effective amount of retinoid herein. Preferably, administration is carried out systemically, very preferably orally and less preferably parenterally. Topical administration is also possible, and in some cases is preferable. Administration is continued as long as benefit is obtained.

For topical administration, "square inch" refers to square inch of body area treated.

The invention is illustrated in the following specific examples.

EXAMPLE I

It is known that when the teratocarcinoma stem cell line F9 is treated with all-trans-retinoic acid (RA) in monolayer culture, the cells differentiate into parietal endodermal-like cells, an extraembryonic type of epithelial cells in the mouse blastocyst. See Gudas, L. J., et al (27). The invention herein involves the conception that effecting this differentiation and determining retinol metabolites and purification thereof would lead to the discovery of biologically active retinoids which heretofore were not known to be biologically active. This example constitutes the experiment based on the conception.

F9 stem cells (ATCC CRL 1720) initially at a concentration of $5 \times 10^6$ cells/plate (each plate with 150 $cm^2$ surface area) were cultured at 37° C. in DME medium, i.e., Dulbicco's Modified Eagle's medium (purchased from ICN Biomedical, catalog number 10-331-22) plus 10% calf serum in the presence of 1 $\mu$M RA for 24 or 48 h. Subsequently, the cells were washed and incubated at 37° C. with 50 nM $^3$H-retinol for 9 h. The media were collected and the cells were rinsed with an isotonic phosphate buffered saline solution in reduced light. Cells were scraped into 500 $\mu$l of PBS and retinoids were extracted immediately according to the method of McClean et al. (15). Briefly, 350 $\mu$l of acetonitrile/butanol (50:50 v/v) containing 50 $\mu$g/ml butylated hydroxy toluene (BHT) was added to 500 $\mu$l of cell or media and then vortexed for 30 sec followed by the addition of 300 $\mu$l of a saturated dibasic potassium phosphate solution and repeated vortexing. Appropriate internal standards were added prior to extraction so that their elution profiles could be followed by absorbance. After centrifugation (10,000×g for 10 min), the organic layer was removed, dried in a Speed-Vac and stored for no more than 3 days at −70° C.

Each sample was dissolved in 180 $\mu$l ethanol for analysis by high pressure liquid chromatography (HPLC). An HPLC system including a photodiode array detector (Waters) was used to separate the various retinoids. An analytical 5-$\mu$m reversed-phase $C_{18}$ column (4.6 mm×25 cm) (Vydac catalog # 201TP54) at flow rate of 1.5 ml/min, with a linear gradient from 40% acetonitrile (ammonium acetate (15 mM, pH 4.7)) to 67% acetonitrile for 35 min followed by 100% acetonitrile for an additional 25 min was employed. An on line scintillation counter (Packard A-500) was used to detect labeled retinoids.

A major change in retinol metabolism is shown in FIG. 1 to occur when F9 stem cells are induced to differentiate by RA. The synthesis of several relatively polar retinol metabolites is induced about 15–20 fold in the cell extracts as well as in the media. This induction of retinol metabolism is seen as early as 12 hours after RA treatment and is maintained as late as 5 days thereafter. It is notable that the rates of synthesis of some retinol derivatives such as 14-hydroxy-4, 14-retro-retinol are unchanged after RA treatment. It is also notable that RA was not detected as an endogenous retinol metabolite in either the F9 stem cells or the RA-treated F9 stem cells. The level of detection of this assay using $^3$H-retinol as a substrate, was calculated to be approximately $10^{-10}$ M. FIG. 1 shows HPLC radiochromatograms of cell extracts from F9 stem cells (denoted "a") and all-trans retinoic acid treated F9 cells (denoted "b"). Retinoids were identified by matching their elution times and their light absorption spectra with those of known standards and by co-injection with known standards.

Since the induced retinol derivatives, retinoids A, B and C (FIG. 1), could not be identified by comparison with known standards, the collection of retinoids from the media and the purification of these induced retinoids were undertaken as described. From 20 liters of incubation media, 60 absorption units at 326 nm of the first pure retinoid and 20 absorption units at 354 nm of the second pure retinoid were isolated. The purification was carried out as follows.

A large quantity of cells (200 plates each with 150 cm$^2$ surface area) was grown in DME medium plus 10% calf serum and then treated with RA (1 μM) for 24 or 48 h. The cells were washed and incubated in the presence of 10 μM retinol for 24 h to maximize the production of the retinol derivatives. The media was then collected and the proteins were precipitated with 60% ammonium sulfate for 6 h. The retinoids were then extracted from the protein pellet as described in McClean et al. (15). After the extraction, a series of reversed-phase columns were employed. These consisted of a preparative $C_{18}$ column of 250 by 22 mm internal diameter (ID) at a flow rate of 8 ml/min with a linear gradient from 45% to 55% acetonitrile in water in 30 min. Next, a semipreparative $C_{18}$ column of 250 by 10 mm ID was employed at a flow rate of 2 ml/min with a linear gradient of 50% acetonitrile to 55% acetonitrile in water in 30 min. The same column was used for a second time at the same flow rate of 2 ml/min but with 60% to 85% methanol in water linear gradient in 30 min. Finally, an analytical $C_4$ column of 250 by 4.6 mm ID was employed as the final step at a flow rate of 1 ml/min with a linear gradient of 45% acetonitrile to 65% acetonitrile in water in 20 min.

Figure 1B:
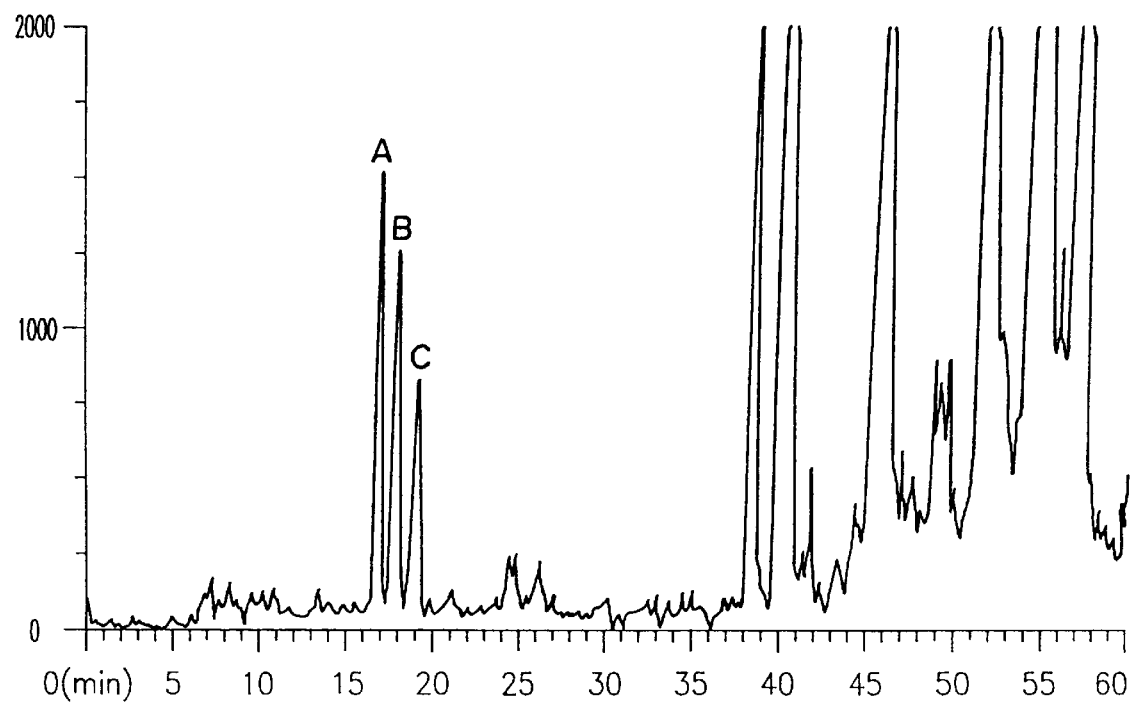

FIG. 2 shows spectra of the retinoids A and C. The CD (circular dichroism) spectrum of retinoid A in methanol is depicted in FIG. 2a (left scale). The UV spectrum of retinoid A in methanol is depicted in FIG. 2a (right scale). The UV spectrum of retinoid C is depicted in FIG. 1(b). About 60 and 20 absorption units of compounds A and C (see FIG. 1) respectively were purified and analyzed by nuclear magnetic resonance (NMR), mass spectroscopy (MS) and circular dichroism (CD). FIG. 2c shows the mass spectrum of retinoid A. FIG. 2d shows the NMR spectrum of retinoid A. FIG. 2e shows the mass spectrum of retinoid C. FIGS. 2f and 2g show NMR spectra of retinoid C.

Figure 2A:
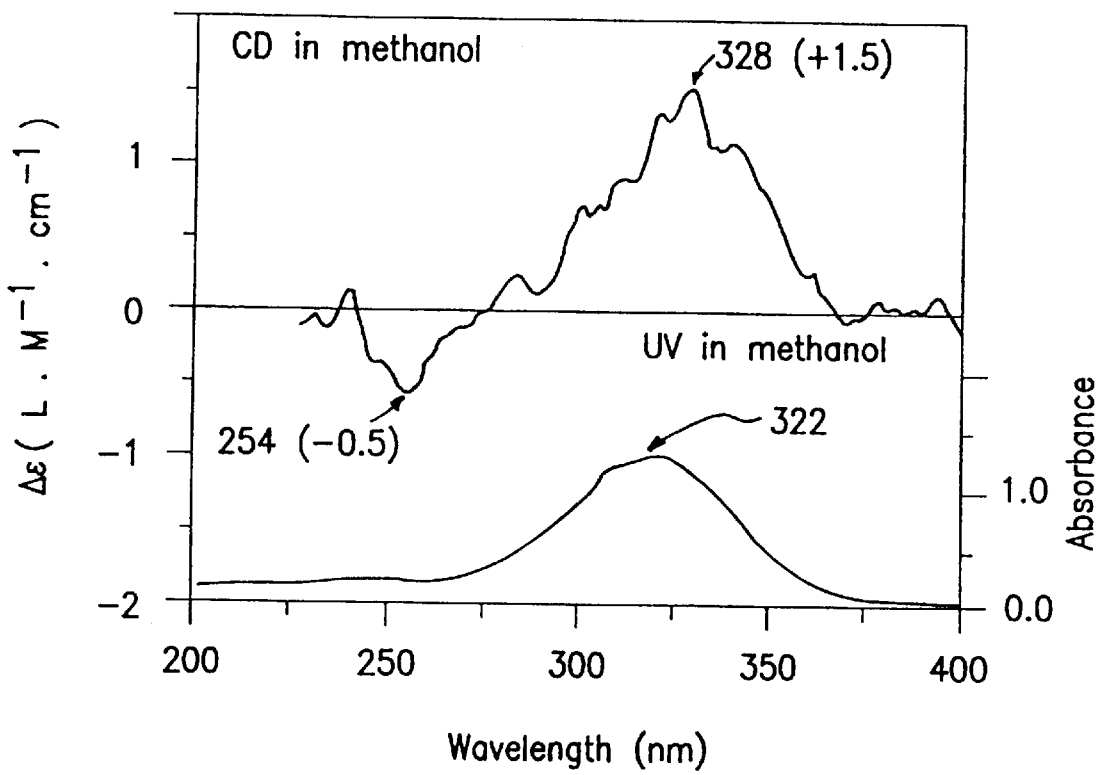
FIGS. 2(a)–2(g) depict spectra of retinoids A and C referred to in FIG. 1 and constitute results of Example I.

Retinoid A exhibited an absorption spectrum with $\lambda_{max}$ at 322 nm (FIG. 2a). The high resolution electron impact mass spectroscopy (EI-MS matrix perfluorokerosine PFK; FIG. 2c) gave an observed value of 302.2234 (calculated for $C_{20}H_{30}O_2$=302.2246), suggesting that retinoid A has one oxygen atom more than its precursor retinol ($C_{20}H_{30}O$), which can be accounted for by an additional hydroxyl group (FIG. 2c). The proton nuclear magnetic spectrum ($^1$H NMR, Varian VXR400 MHZ; solvent CDCl$_3$, chemical shift δ in ppm, coupling constants J in Hertz; FIG. 2d) presents the following signals: δ 1.03/1.06 [2s, 6H, 1-(CH$_3$)2], 1.84 (s, 3H, 5-CH$_3$), 1.88 (s, 3H, 13-CH$_3$), 1.96 (s, 3H, 9-CH$_3$), 4.02 (m, 1H, 3-H), 4.33 (t, J 7.5, 2H, 15-H), 5.71 (t, J 7.2, 1H, 14-H), 6.10 (d, J 16, 1H, 8-H), 6.12 (d, J 11, 1H 10-H), 6.17 (d, J 16, 1H, 7-H), 6.31 (d, J 15, 1H, 12-H), 6.61 (dd, J 11, 15, 1H, 11-H) (FIG. 2d). These spectroscopic data, in agreement with literature data as set forth in Vetter, W., et al (28), established retinoid A as all-trans-4-hydroxy-retinol.

The carbon at position 4 is an asymmetric center. Thus naturally occurring 4-hydroxy-retinol might be optically active. Indeed, its CD spectrum (FIG. 2a) shows two Cotton effect bands at 328 nm (δε+1.5), and 254 nm (δε−0.5). The absolute configuration at C-4 was determined by synthesis as (4S); thus, the hydroxyl group at position 4 has a β configuration. This establishes that retinoid A is all-trans-(4S)-4-hydroxy-retinol.

Retinoid B (FIG. 1(b)) was later determined to be 13-cis-4-hydroxyretinol isomer by matching its elution time and UV spectrum with that of a standard.

Figure 2B:
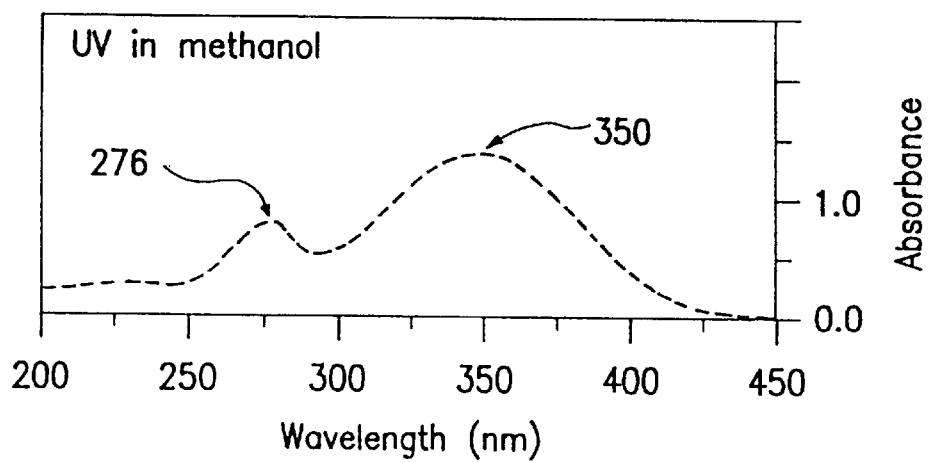
Figure 2C:
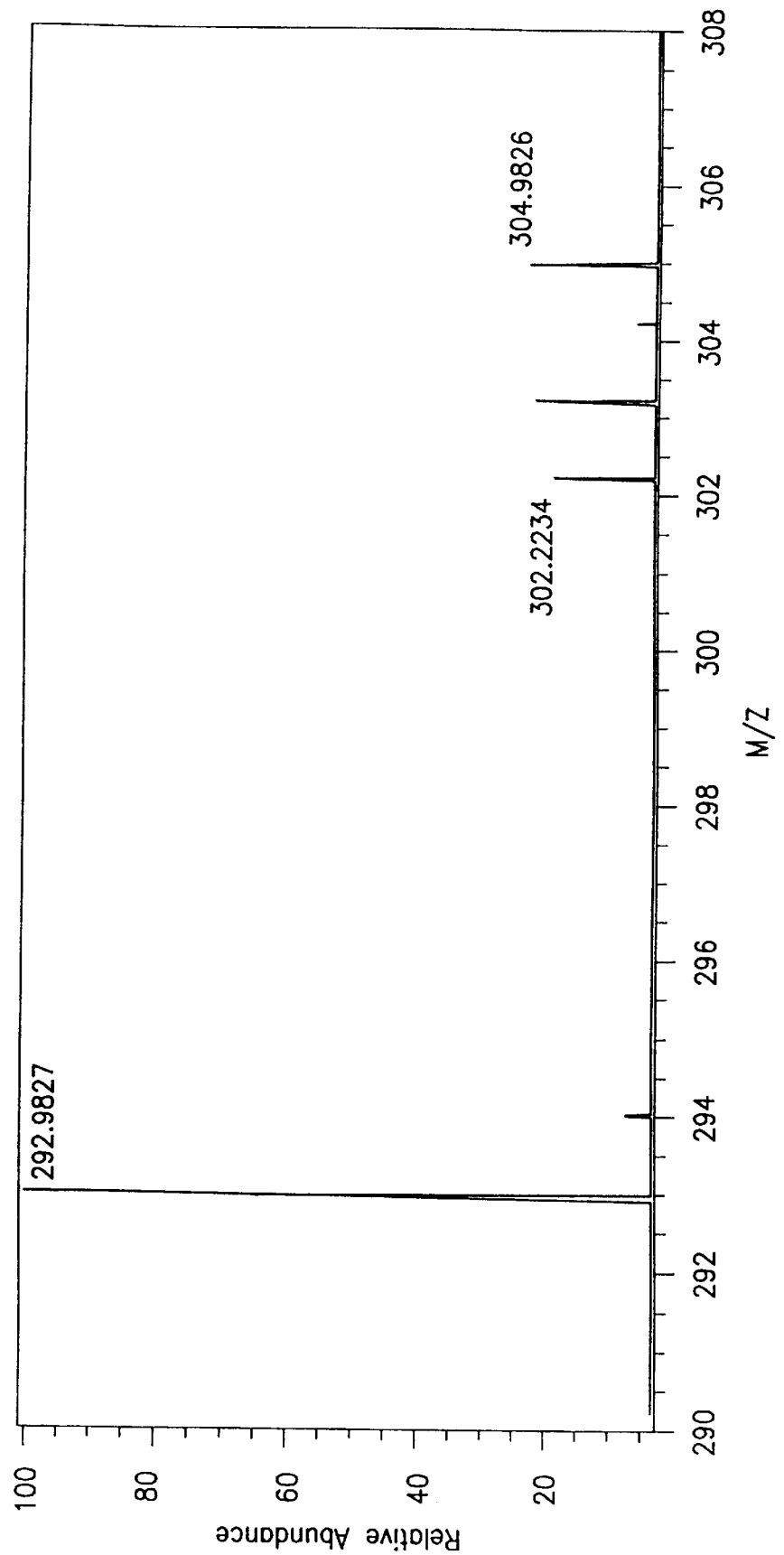
Figure 2D:
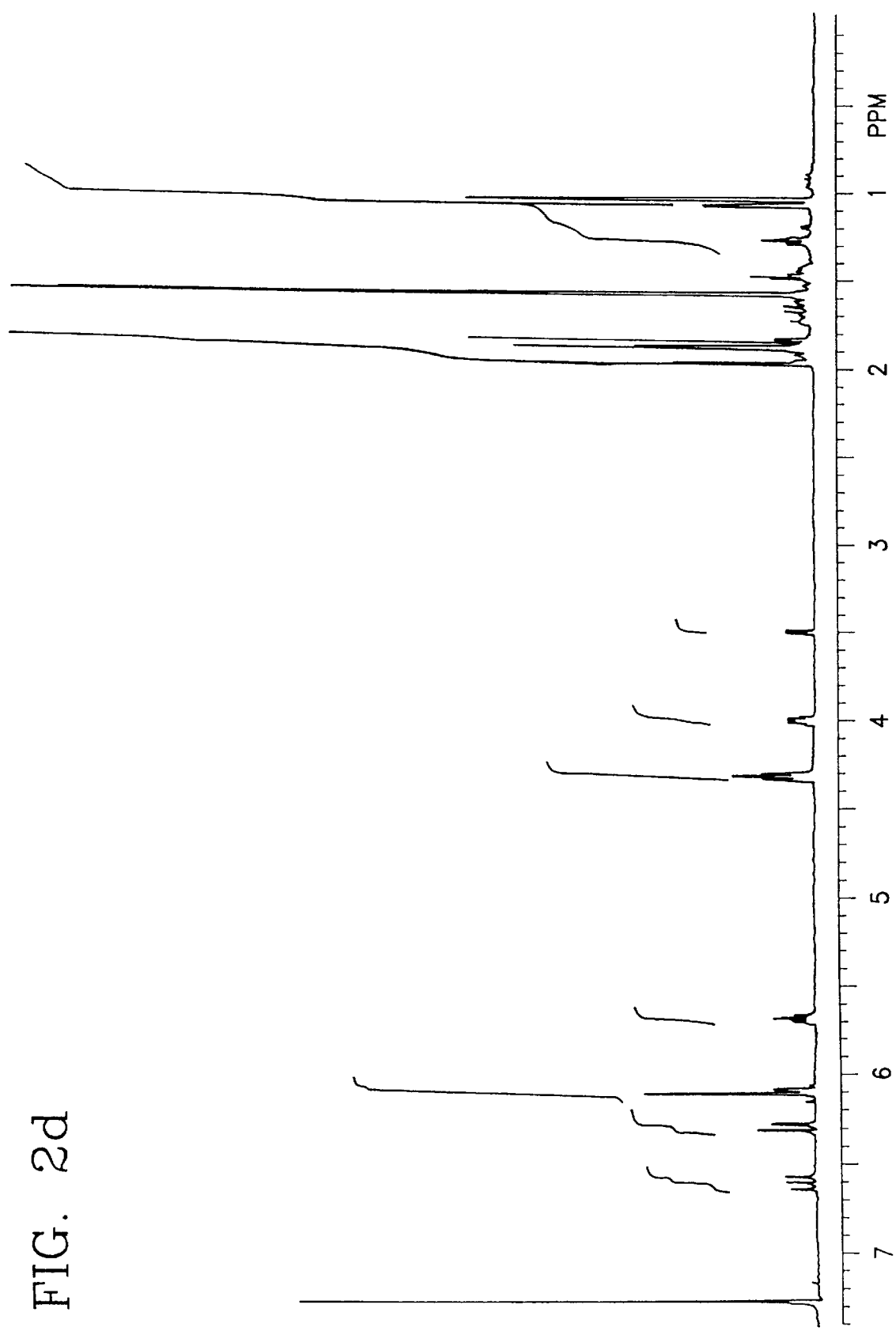
Figure 2E:
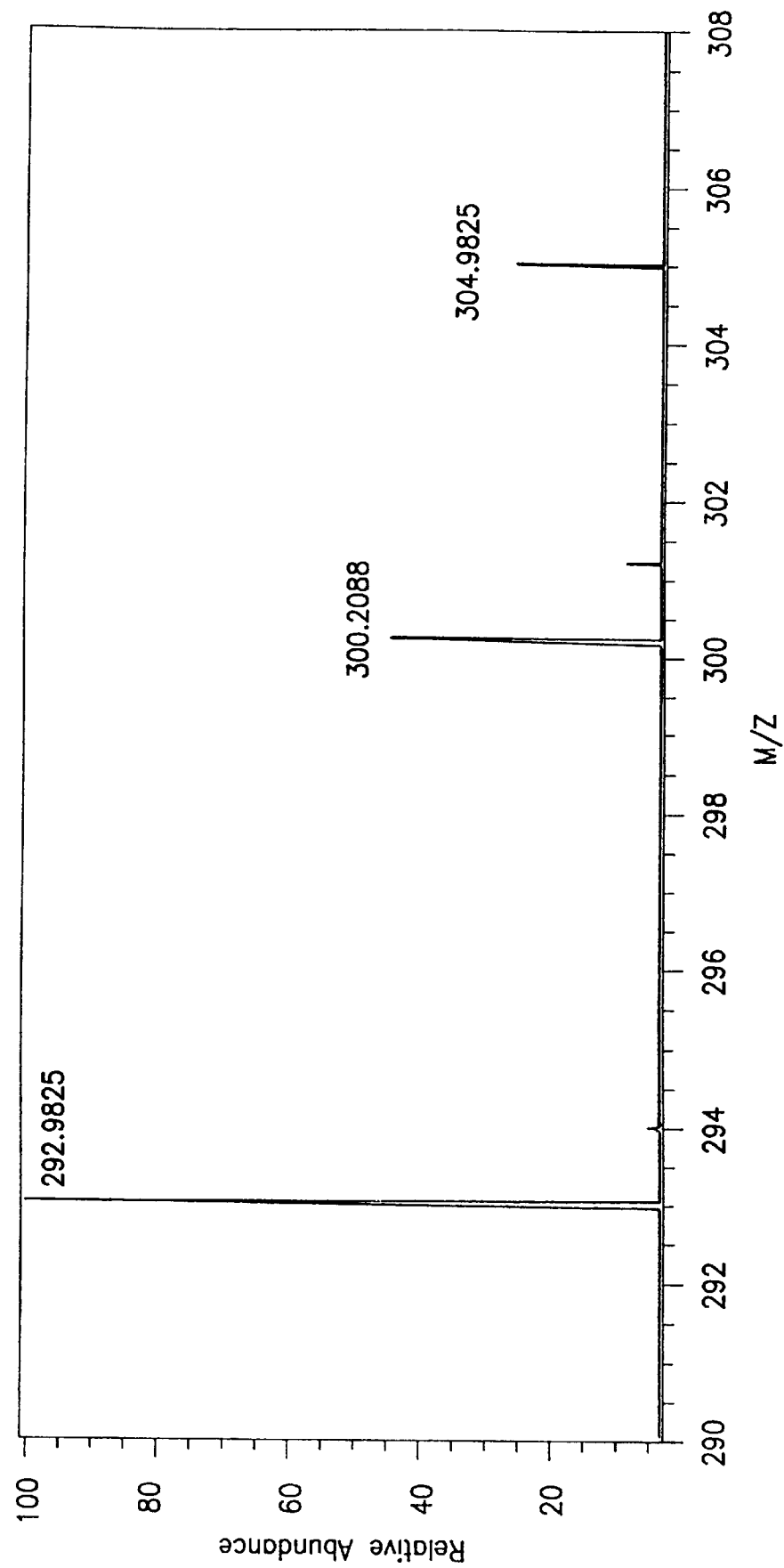
Figures 2F, 2G:
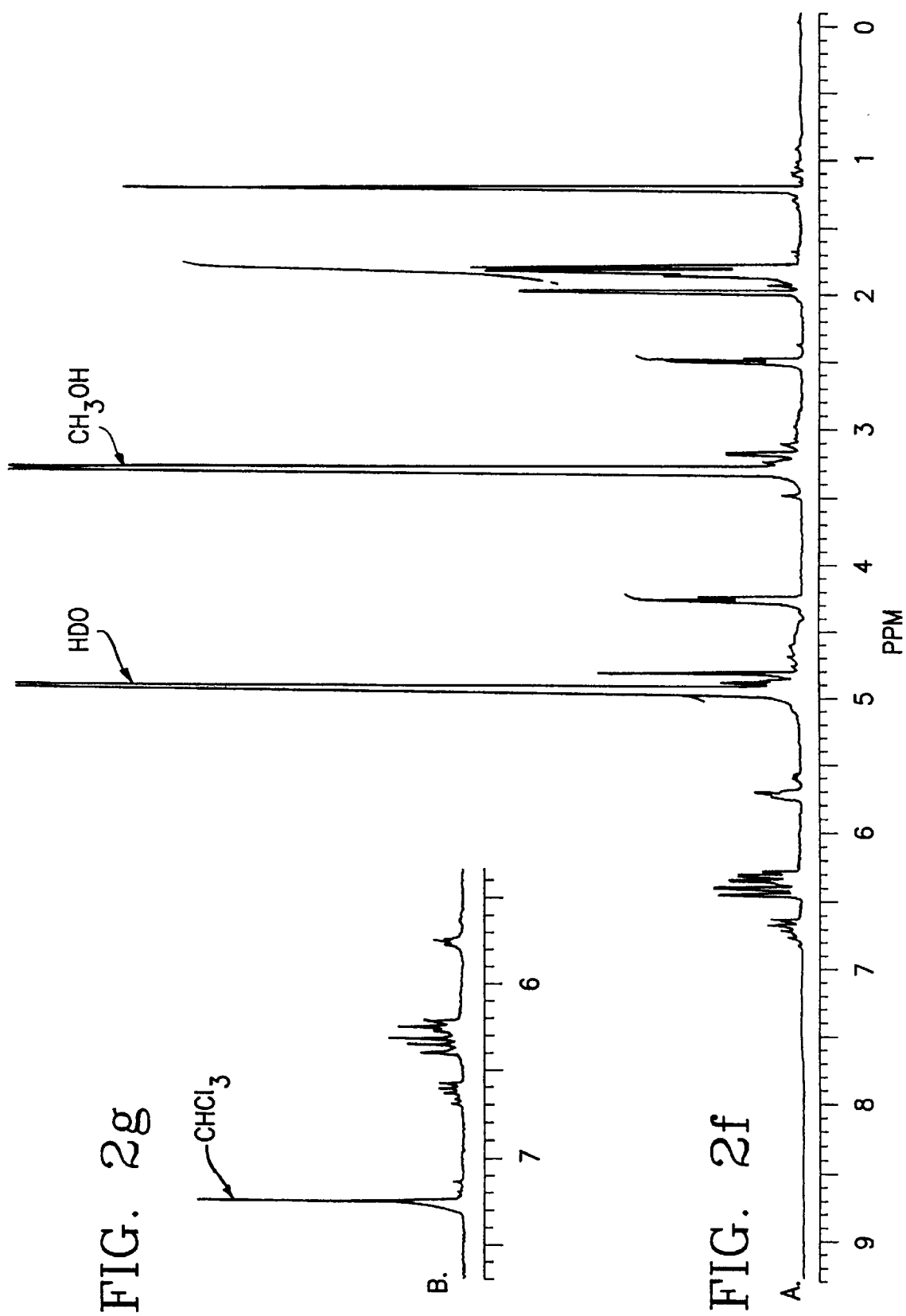

Retinoid C exhibited an absorption spectrum with $\lambda_{max}$ at 276 and 350 nm (FIG. 2b). The high resolution electron impact mass spectrum (EI/MS, matrix perfluorokerosine PFK), FIG. 2e, gave an observed value of 300.2088 (calculated for $C_{20}H_{28}O_2$=300.2090), indicating that this retinoid has two hydrogen atoms less and one oxygen atom more than its precursor retinol. This data, the red shifted UV $\lambda_{max}$ (350 nm as compared to 322 nm for retinol), and the band at 276 nm suggest a keto group at position 4. The proton nuclear magnetic resonance spectrum ($^1$H NMR, solvent CDCl$_3$, chemical shift δ in ppm, coupling constants J in Hertz; FIG. 2f) presents the following signals: δ ppm 1.15 [s, 6H, 1-(CH$_3$)$_2$], 1.82 (t, J 7, 2H, 2-H$_2$), 1.82 (s, 3H, 5-CH$_3$), 1.84 (s, 3H, 13-CH$_3$), 1.95 (s, 3H, 9-CH$_3$), 2.48 (t, J 7, 2H, 3-H$_2$), 4.32 (t, J 7, 2H, 15-H$_2$), 5.72 (t, J 7, 1H, 14-H), 6.21 (d, J 15, 1H, 7-H), 6.22 ( d, J 10, 1H, 10-H), 6.31 (d, J 15, 1H, 8-H), 6.35 (d, J 15.2, 1H, 12-H), 6.59 (dd, J 15.2, 10, 1H, 11-H) (FIG. 2f). These spectroscopic data establish retinoid C as all-trans-4-oxo-retinol.

EXAMPLE II

Retinoids were assayed for their ability to bind members of the family of the retinoic acid receptors, the RARs, as follows:

COS-1 cells were transfected by DEAE-dextran with pSG5 expression vectors containing cDNAs for mouse RARs α, β, or γ or RXRs α, β, or γ. See Levin, A. A., et al (29). Nucleosol or cytosol fractions were prepared as described in Nervi, C., et al (30) and Nervi, C., et al (31) and stored at −70° C. until use. Aliquots of nucleosol or cytosol were incubated in nuclei lysis buffer as described in Nervi, C., et al (30) with tritiated ligands for 4 h at 4° C. Retinoids were added in ethanolic solutions that did not exceed 2% of the total incubation volume. For competitive binding assays, the incubations were performed with increasing concentrations of unlabeled competing ligand and a fixed concentration of the radioligand (10 nM $^3$H-retinoic acid). In saturation kinetic studies, incubations were performed in the presence of increasing concentrations of the indicated radioligand. For all binding assays, bound was separated from free radioactivity as described in Levin, A. A., et al (29).

To determine whether 4-hydroxyretinol and 4-oxo-retinol are ligands for RARs, their ability to compete for binding sites with all-trans-retinoic acid was examined under equilibrium conditions as described in Allenby, G., et al (32). The results are set forth in Table I below wherein 4-oxo-retinol stands for all-trans-4-oxo-retinol, 4-OH retinol stands for all-trans-4-hydroxyretinol, RA stands for all-trans-retinoic acid and wherein IC$_{50}$ is the concentration to inhibit 50% binding of $^3$H-all-trans-retinoic acid.

TABLE I

| Ligand | IC$_{50}$ RAR-α | IC$_{50}$ RAR-β | IC$_{50}$ RAR-γ |
|---|---|---|---|
| 4-oxo-retinol | 330 ± 54[1] | 420 ± 110 | 3200 ± 520 |
| 4-OH retinol | 5000 ± 1400 | 3800 ± 1100 | 3400 ± 1600 |
| RA[2] | 5 ± 02 | 5 ± 0 | 4 ± 1 |

TABLE I-continued

| Ligand | IC$_{50}$ RAR-α | IC$_{50}$ RAR-β | IC$_{50}$ RAR-γ |
|---|---|---|---|
| 4-oxo-retinoic acid | 120 | 210 | 350 |

[1] Results presented are the mean and IC$_{50}$ (± SD) in nM of at least 3 replicate experiments performed in duplicate.
[2] Data from Allenby, G., et al (32) provided for comparison purposes.

The results indicate that 4-hydroxyretinol is a relatively weak inhibitor of $^3$H-all-trans-retinoic acid binding to all three subtypes of retinoic acid receptors (RARs) as indicated by the IC$_{50}$ values (Table 1). The results show that all-trans-4-oxo-retinol is a strong inhibitor of $^3$H-retinoic acid binding to RAR-α and RAR-β and a weaker inhibitor (10-fold less) of $^3$H-retinoic acid binding to RAR-γ. Thus, all-trans-4-oxo-retinol appears to be the first endogenous retinoid discovered to exhibit preferential (selective) binding to subtypes of RARs, and the first retinoid to bind the RARs which has an CH$_2$OH group rather than a COOH group at the end of the side chain. It is important to note that the intracellular concentration of all-trans-4-oxo-retinol in differentiating F9 stem cells was calculated to be approximately 85 nM, enough to bind and activate RAR-α and RAR-β.

Neither the 4-hydroxyretinol nor the 4-oxo-retinol inhibited the binding of $^3$H-9-cis retinoic acid to the RXRs (data not shown).

Retinol, the precursor for 4-oxo-retinol, produced no apparent inhibition of all-trans-$^3$H-retinoic acid binding to any of the RARs or $^3$H-9-cis retinoic acid binding to the RXRs even when used at concentrations of up to 50,000 nM.

Both 4-hydroxyretinol and 4-oxo-retinol were unable to inhibit the binding of all-trans-$^3$H-retinoic acid to cellular retinoic acid binding protein I (CRABP I) (data not shown).

EXAMPLE III

Figure 3:
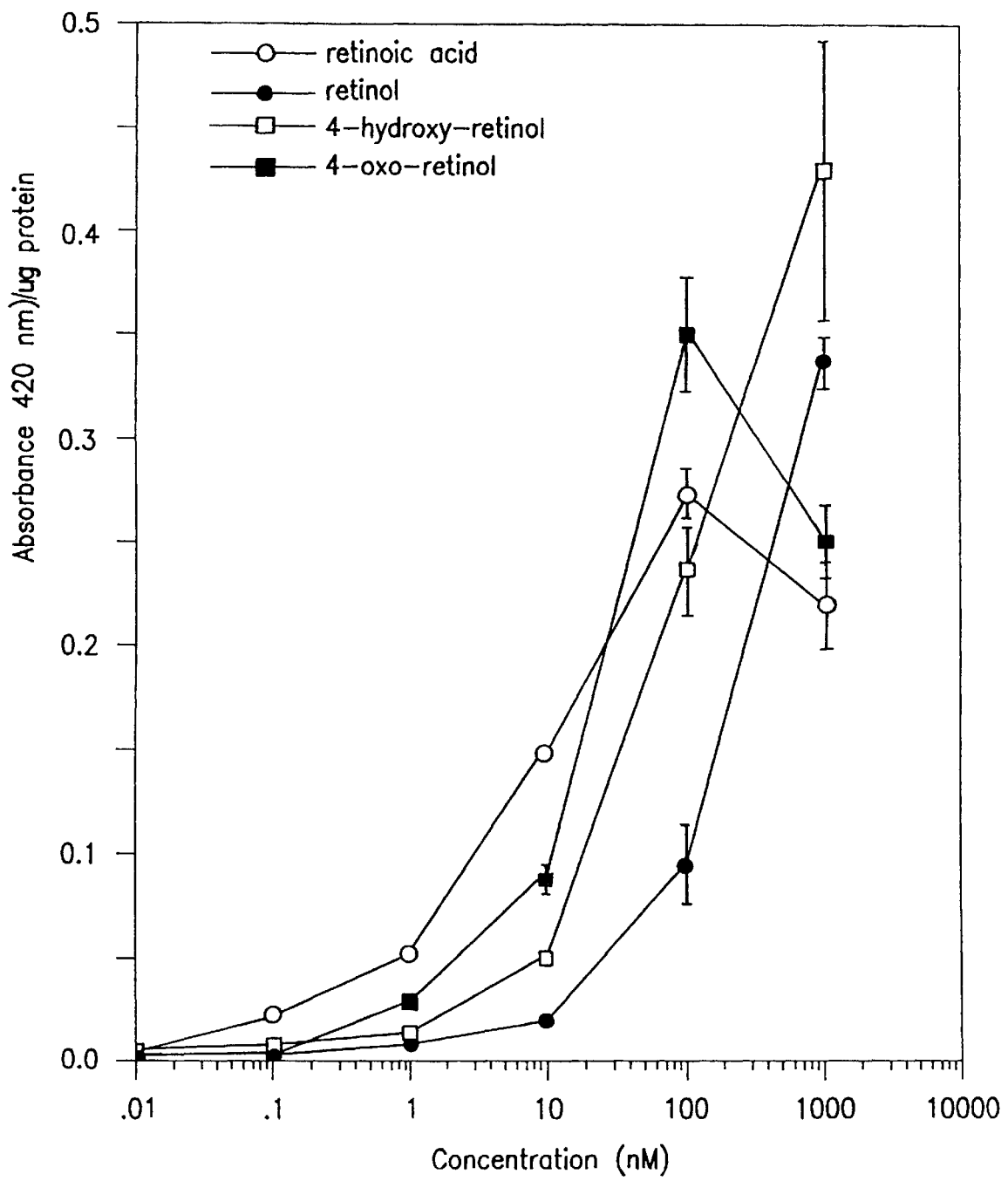
FIG. 3 depicts dose response curves for the F9-RARE-β-galactosidase reporter cell line when treated with pure, synthetic compounds as denoted and sets forth results of Example III.
Figure 5A:
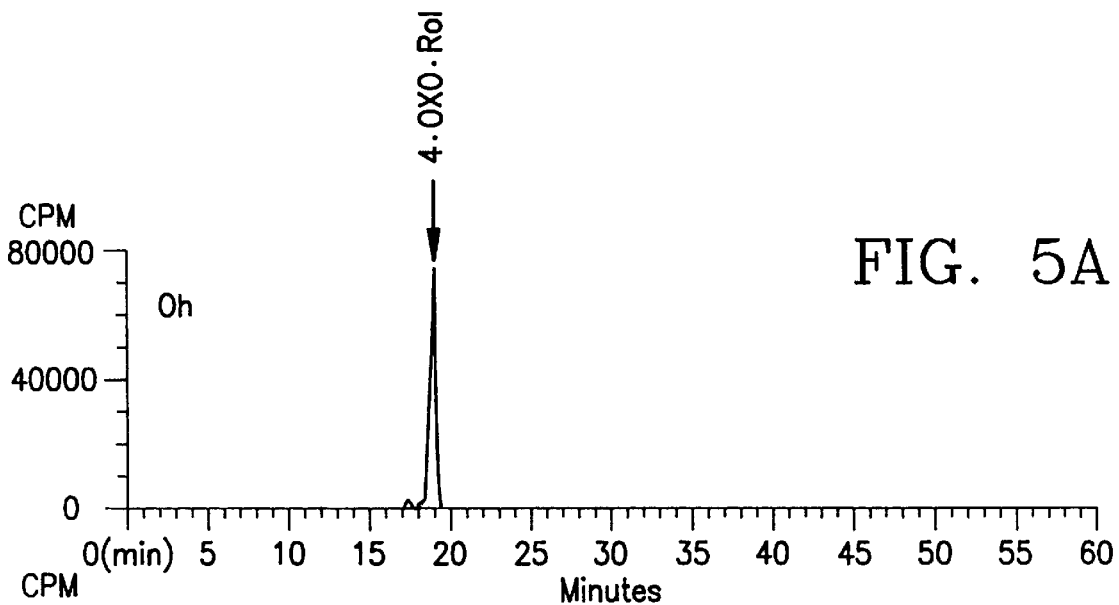
In FIGS. 5A–5D, "4-OXO-ROl" stands for all-trans-4-oxo-retinol and "CPM" stands for counts per minute of tritium.
Figure 5B:
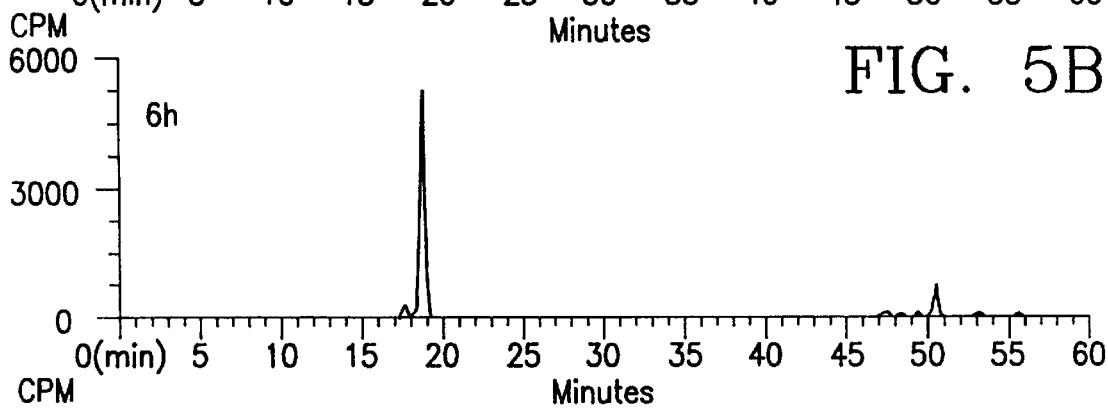
Figure 5C:
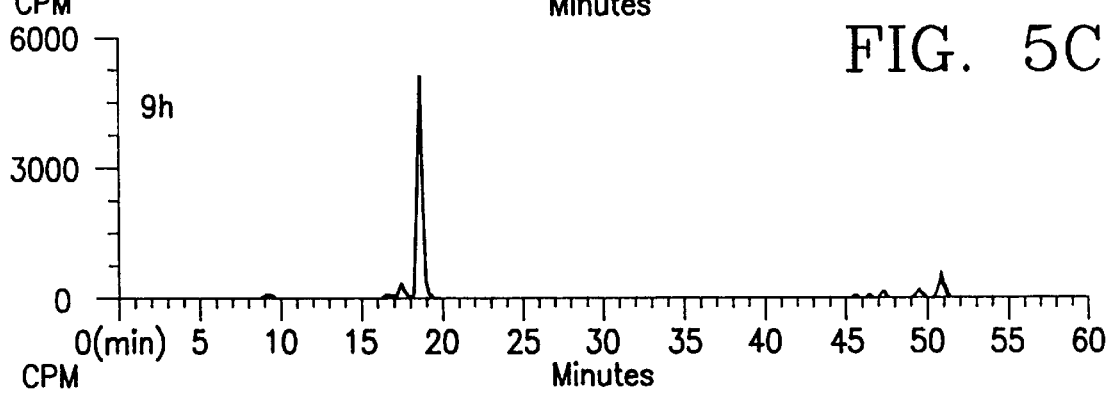
Figure 5D:
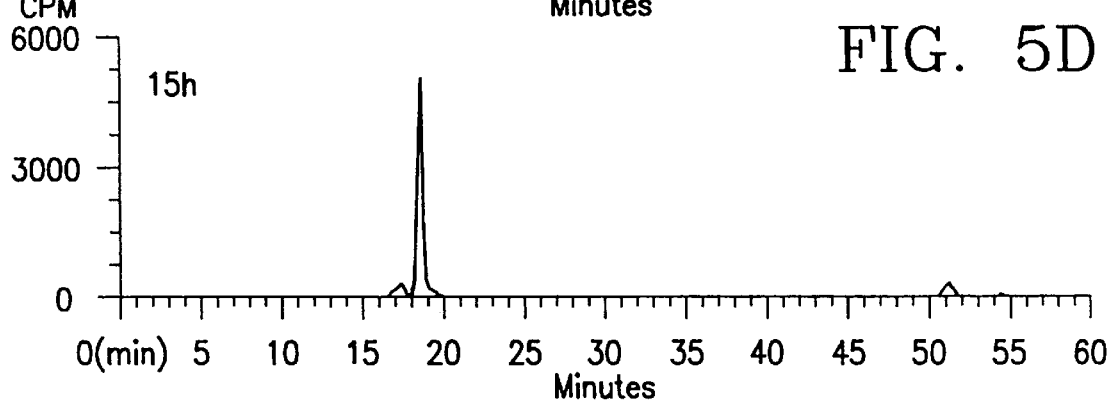

To determine the efficiency of various retinoids in inducing transcription of the reporter gene RARE-β-galactosidase F9-RARE-β-galactosidase reporter cell line which is described in Wagner, M., et al (33), dose response curves of retinol, all-trans-4-hydroxyretinol, 4-oxo-retinol, and retinoic acid were prepared using the F9-RARE-β-galactosidase reporter cell line. Cells were treated with different concentrations of retinoids in media lacking serum, harvested and assayed for β-galactosidase activity. The activities measured in response to the various retinoids are shown in FIG. 3 wherein each point is the mean ±SE of three separate measurements. The β-galactosidase activity in this cell line reflects the activation of the RARs. The response to retinoic acid and retinol is similar to what was reported earlier as described in Wagner, M., et al (33). As expected, this reporter cell line responded to low concentrations of retinoic acid but only to high concentrations of retinol. The activity attributed to high concentrations of retinol in this assay is most likely due to its conversion to 4-hydroxyretinol and 4-oxo-retinol. The all-trans-4-hydroxyretinol was moderately more active than retinol while 4-oxo-retinol was a good inducer of activity. Using this assay, all-trans-4-oxo-retinol and all-trans-4-hydroxyretinol had EC$_{50}$ values of 42 nM and 76 nM, respectively as compared with 9 nM for retinoic acid and with >3000 nM for retinol. These results indicate that 4-oxo-retinol is a potent activator of an RARE which requires binding and activation of at least one subtype of the RARs.

EXAMPLE IV

Teratocarcinoma stem cells can be induced to differentiate in monolayer culture by retinoic acid over a 3–4 day period into nonmalignant endoderm cells resembling the extraembryonic endoderm of the mouse blastocyst as described in Gudas, L. J., et al (27). The F9 teratocarcinoma stem cell line is used as a model tumor cell differentiation system because F9 stem cells share similar biochemical, immunological and morphological characteristics with early mouse embryonic stem cells and additionally, large numbers of cells can be cultured and experimentally manipulated. The expression of several homeobox genes including Hoxa-1 is induced by RA in mouse teratocarcinoma cell lines as described in LaRosa, G. J., et al (34) and LaRosa, G. J., et al (35). Hoxa-1 transcripts are rapidly induced in retinoic acid treated F9 stem cells even in the absence of new protein synthesis, and the magnitude of expression is proportional to the retinoic acid concentration to which the cells are exposed. See LaRosa, G. L, et al (34). Other genes such as laminin B1 are activated subsequent to the activation of Hox 1.6 by retinoic acid as described in Vasios, G. W., et al (36).

Since 4-hydroxyretinol and 4-oxo-retinol are endogenous metabolites of retinol in F9 stem cells whose levels are upregulated during retinoic acid-induced differentiation and since, in addition, 4-oxo-retinol appears to bind with good affinity to RAR-α and RAR-β and can activate an RARE-reporter gene in F9 stem cells, the effect of these retinoids on F9 stem cell differentiation was tested as follows: Cells were treated with 1 μM concentration of retinoid as described for 24, 48 and 72 hours and gene expression of Hoxa-1 and laminin B1 was monitored by Northern blot analysis. Hoxa-1 transcripts were induced 4, 9, 17, and 25 fold by retinol, all-trans-4-hydroxyretinol, all-trans-retinoic acid and all-trans-4-oxo-retinol, respectively, at 72 h after retinoid treatment. Laminin B1 expression was induced 2, 3, 7, and 9 fold by retinol, all-trans-4-hydroxyretinol, all-trans-4-oxo-retinol, and all-trans-retinoic acid, respectively, at 72 h after treatment. This assay shows that both 4-hydroxyretinol and 4-oxo-retinol are able to elicit the same effect on F9 stem cell differentiation markers as retinoic acid, but to different extents.

EXAMPLE V $^3$H-4-hydroxyretinol and $^3$H-4-oxo-retinol were purified from RA treated, differentiated F9 cells (ATCC CRL 1720) after the differentiated cells were incubated with $^3$H-retinol for 18 h. The identities of purified $^3$H-4-hydroxyretinol and $^3$H-4-oxo-retinol were verified by matching both the elution times on the HPLC and the spectra of known standards.

F9 stem cells or retinoic acid-treated cells (72 h) were cultured in the presence of 50 nM of either $^3$H-4-hydroxyretinol or $^3$H-4-oxo-retinol for different periods of time.

FIGS. 4A–4D depict HPLC analysis after incubation in the presence of 50 nM $^3$H-4-hydroxyretinol for periods of time as indicated and extraction using the method described in McClean, S. W., et al (15). F9 stem cells are shown in FIGS. 4A–4D to convert 4-hydroxyretinol to 4-oxo-retinol. The rate of this conversion was virtually identical in both stem and retinoic acid-treated cells. This rate was calculated to be about 20% in a period of 15 h. No other metabolite, including no 4-oxo-all-trans-retinoic acid, was detected in this assay.

FIGS. 5A–5D depict HPLC analysis after incubation in the presence of 50 nM $^3$H-4-oxo-retinol for periods of time as indicated and extraction using the method described in McClean, S. W., et al (15). The results are the same in both stem and retinoic acid- treated cells. As shown in FIGS. 5A–5D, the metabolism of 4-oxo-retinol in F9 stem cells was very slow resulting in a very long half-life. The half-life of 4-oxo-retinol is on the order of days in F9 stem cells, as indicated by the 4-oxo-retinol peak height remaining the same. The only detected metabolites of 4-oxo-retinol in F9 stem cells were small amounts of several very hydrophobic retinoids which are presumed to be 4-oxo-retinyl esters. No 4-oxo-retinoic acid was detected in a period up to 15 h. This was not surprising since 4-oxo-retinoic acid has a distinct UV spectrum which was not observed when F9 retinol derivatives were analyzed previously.

All-trans-retinoic acid has a half-life of 3 hrs. in these F9 stem cells as described in Williams, J. B., et al (37) and Boylan, J. F., et al (38). In differentiated retinoic acid-treated F9 stem cells an enzyme is induced which breaks down all-trans-retinoic acid so the half-life is much shorter than 3 hr. as is described in Williams, J. B., et al (37) and Boylan, J. F., et al (38). In contrast, 4-oxo-retinol appears to be equally stable in F9 stem or differentiating cells and is shown in FIG. 5 to have a half-life of more than 15 hours.

These results indicate that 4-hydroxyretinol is an intermediate in the synthesis of 4-oxo-retinol from retinol in F9 stem cells. They also suggest that at least part of the activity associated with 4-hydroxyretinol may be due to its enzymatic conversion to 4-oxo-retinol. While the level of all-trans-4-hydroxyretinol was increased by retinoic acid treatment (FIG. 1), the rate of conversion of 4-hydroxyretinol to all-trans-4-oxo-retinol was not affected by retinoic acid treatment. This result shows the conversion of retinol to 4-hydroxyretinol is the rate limiting step.

EXAMPLE VI

Patients with morphologic diagnostic criteria for acute promyelocytic leukemia (M3 or M3 variant subtype) by karyotyping or PCR analysis, including the b(15;17) (q22; q12-21) translocation, are treated with oral all-trans-4-oxo-retinol at a dose of 100 mg/square meter of body surface area per day. The drug is formulated in soft gelatin capsules which are administered once or twice a day to provide the dose as stated. The drug is administered for 40 to 60 days until remission induction occurs as indicated by normal karyotype, disappearance of coagulation abnormalities (e.g., increased platelet count and plasma fibrinogen level), observation of differentiation of cancer cells and the appearance of mature granulocytic markers in cell surface immunophenotyping, as indicated by reduced number of cells expressing CD33 and greater portion of cells expressing CD16. Patients with newly diagnosed disease then receive all-trans-4-oxo-retinol for 30 days after remission induction; then, either conventional consolidation therapy (e.g., cytosine arabinoside) or continued treatment with all-trans-4-oxo-retinol alone is continued. During remission induction, liver function tests are performed and serum cholesterol and triglycerides are measured twice a week and bone marrow aspiration is performed once a week until complete remission or failure is documented. Long term cures are considered to be obtainable.

When all-trans-4-hydroxyretinol is substituted for the all-trans-4-oxo-retinol at a dose of 100 mg/square meter of body surface per day, similar results of long term remission and cures are obtained.

When 7-cis, 9-cis, 11-cis and 13-cis isomeric forms of 4-oxo-retinol and 4-hydroxyretinol are substituted for the all-trans isomers in the same dosages, similar results are obtained. When the compounds with various $R_1$ groups described above are substituted for the all-trans-4-oxo-retinol, similar results are obtained. When the ester and aldehyde forms are used in place of the alcohol form, therapeutic results similar to what are obtained with the alcohol form are obtained.

EXAMPLE VII

Current systemic chemotherapy regimens are unable to prolong survival of patients with advanced head and neck cancer. Patients treated with all-trans-4-oxo-retinol or all-trans-4-hydroxyretinol at oral doses of 100 mg/square meter of body surface area per day survive beyond the median of 4–6 months,and/or have reduced tumor burden during the period during which drug is administered.

EXAMPLE VIII

Patients with breast cancer treated with all-trans-4-oxo-retinol or all-trans-4-hydroxyretinol at oral doses of 100 mg/square meter of body surface area per day have a reduced tumor burden during the time during which the drug is given.

EXAMPLE IX

Patients with deep (cystic) acne treated with all-trans-4-oxo-retinol or all-trans-4-hydroxyretinol at an oral dose of 100 mg/square meter of body surface per day have a greater than 85% mean reduction in lesion counts at the end of a 3 to 6 month treatment period and in some cases complete clearance occurs after discontinuation of therapy. A very prolonged remission, and potentially permanent cure can be obtained.

EXAMPLE X

Patients with psoriasis vulgaris, pustular psoriasis, or erythrodermic psoriasis are treated with long term continuous administration of all-trans-4-oxo-retinol or all-trans-4-hydroxyretinol at an oral dosage of 50 mg/square meter of body area per day as the only treatment or in combination with conventional treatment with PUVA (psoralen plus long wave UV light), or in combination with conventional treatment with Vitamin D analogs, corticosteroids, methotrexate, or cyclosporine. Once the psoriasis has improved, patients may stop retinoid therapy or be given long term retinoid or UV maintenance therapy.

Patients with psoriatic arthritis treated with an oral dose of all-trans-4-hydroxyretinol or all-trans-4-oxo-retinol in a dosage of 50 mg/square meter of body area per day exhibit fewer tender joints and a decreased duration of morning stiffness.

EXAMPLE XI

Treatment of patients with aging or photodamaged skin with all-trans-4-hydroxyretinol or all-trans-4-oxo-retinol orally in a dosage of 100 mg/square meter of body area per day or topically in a dosage of 10 mg per square inch per day over a 4 to 8 month period have fewer and reduced depth of wrinkles, increased smoothness of the skin, and a reduction in pigmented areas of the skin.

When 7-cis, 9-cis, 11-cis and 13-cis isomeric forms of 4-oxo-retinol and 4-hydroxyretinol are substituted for the all-trans forms in the same dosages, therapeutic results similar to what are obtained with the all-trans forms are obtained in Examples VII, VIII, IX, X and XI. When compounds with the various $R_1$ groups described above are substituted for 4-oxo-retinol and 4-hydroxyretinol in the same dosages, therapeutic results similar to what are obtained with 4-oxo-retinol and 4-hydroxyretinol are obtained in Examples VII, VIII, IX, X and XI. When the ester and aldehyde forms are used in place of the alcohol form, therapeutic results similar to what are obtained with the alcohol form are obtained.

Many variations of the above will be obvious to those skilled in the art.

For example, the treatments herein can be employed alone or in combination therapy including but not limited to combination therapy with biological response modifiers, such as interferons; growth factors; vitamins; hormones; intracellular signalling molecules such as cyclic AMP; cytotoxic cancer chemotherapeutic drugs; other retinoids, such as all-trans-retinoic acid; and for psoriasis, PUVA (psoralen plus long wave UV light) treatments.

Because of the variations which will be obvious to those skilled in the art, the invention is defined by the claims.

The full citations are given below of the references cited in abbreviated form above.

REFERENCES

1. Sporn, M. B. and Roberts, A. B. (1985) What is a retinoid? Ciba Found. Symp. 113: 1–5.
2. Gudas, L. J. (1994) Retinoids and vertebrate development. J. Biol. Chem. 269: 15399–15402.
3. Leo, M. A. and Lieber, C. S. (1985) New pathway for retinol metabolism in liver microsomes. J. Biol. Chem. 260: 5228–5231.
4. Warrell, R. P., Jr., Frankel, S. R., Miller, W. H., Jr., Scheinberg, D. A., Itri, L. M., Hittelman, W. N., Vyas, R., Andreff, M., Tafufi, A., Jakubowski, A., Gabrilove, J., Gordon, M. S., and Dmitrovsky, E. (1991) Differentiation therapy of acute promyelocytic leukemia with tretinoin (all-trans-retinoic acid). N. Engl. J. Med. 324: 1385–1393.
5. Warrell, R. P., Jr., de Thé, H., Wang, Z.-Y., and Degos, L. (1993) Acute promyelocytic leukemia. N. Engl. J. Med. 329: 177–189.
6. Lefebvre, P. P., Thomas, G., Gourmel B., Agadir, A., Castaigne, S., Dreux, C., Degos, L., and Chomienne, C. (1992) Pharmacokinetics of oral all-trans-retinoic acid in patients with acute promyelocytic leukemia. Leukemia 5: 1054–1058.
7. Muindi, J. R., Frankel, S. R., Huselton, C., De Grazia, F., Garland, W. A., Young, C. W., and Warrell, R. P, Jr. (1992) Clinical pharmacology of oral all-trans-retinoic acid in patients with acute promyelocytic leukemia. Cancer Res. 52: 2138–2142.
8. Brazzell, R. K., Vane, F. M., Ehmann, C. W., and Colburn, W. A. (1983) Pharmacokinetics of isotretinoin during repetitive dosing to patients. Eur. J. Clin. Pharmacol. 24: 695–702.
9. Hong, W. K., and Itri, L. M. (1994) Retinoids and human cancer. In The Retinoids: Biology, Chemistry and Medicine. M. B. eds., A. B. Roberts, and D. S. Goodman, Raven Press: New York, 597–630.
10. Lippman, S. M., Kavanagh, J. J., Paredes-Espinoza, M., Delgadillo-Madrueno, F., Paredes-Casillas, P., Hong, W. K., Holdener, E., and Krakoff, I. H. (1992) 13-cis retinoic acid plus interferon α-2a: highly active systemic therapy for squamous cell carcinoma of the cervix. J. Natl. Cancer Inst. 84: 241–245.
11. Lippman, S. M., Parkinson, D. R., Itri, L. M., Weber, R. S., Schantz, S. P., Ota, D. M., Schusterman, M. A., Krakoff, I. H., Gutterman, J. U., and Hong, W. K. (1992) 13-cis retinoic acid and interferon α-2a: effective combination therapy for advanced squamous cell carcinoma of the skin. J. Natl. Cancer Inst. 84: 235–241.
12. Peck, G. L. and DiGiovanna, J. J. (1994) Synthetic retinoids in dermatology. In The Retinoids: Biology, chemistry and Medicine. M. B. Sporn, A. B. Roberts, and D. S. Goodman, eds. Raven Press: New York, 631–658.
13. Rafai, E. S., Griffiths, C. E. M., Ditre, C. M., Finkel, L. J., Hamilton, T. A., Ellis, C. N., and Voorhees, J. J. (1992) Topical tretinoin (retinoic acid) treatment for liver spots associated with photodamage. N. Engl. J. Med. 326: 368–374.
14. Mangelsdorf, D. J., Umesono, K., and Evans, R. M. (1994) The retinoid receptors. In The Retinoids: Biology, Chemistry and Medicine. M. B. Sporn, A. B. Roberts, and D. S. Goodman, eds. Raven Press: New York, 319–350.
15. McClean, S. W., Ruddel, M. E., Gross, E. G., Degiovanna, J., and Peck, G. L. (1982) Liquid chromatographic assay for retinol (vitamin A) and retinol analogs in therapeutic trials. Clin Chem. 284: 693–696.
16. Boehm, M. F., Gawinowicz, M. A., Foucault, A., Derguini, F., and Nakanishi, K. (1990) Photoaffinity labeling studies of bacteriorhodopsin with [15-$^{3}$H]-3-diazo-4-keto-all-trans-retinal. J. Am. Chem. Soc. 112: 7779–7782.
17. Henbest, H. B., Jones, E., and Owen, T. C. (1957) Studies in the polyene Series. Part LII. Oxidation of vitamin A and retinene by manganse dioxide. J. Chem. Soc. 4909–4912.
18. Reedy, A. J. (Jun. 9, 1967) Procédé de synthese du 4-hydroxy-retinal. Fr. Patent 1, 484, 573. Chem. Abstr. (1968) 68: 29903m.
19. Surmatis, J. D. (Mar. 28, 1967) Intermediates for the preparation of a carotenoid. U.S. Pat. No. 3,311,656. Chem. Abstr. (1967) 67: 22052d.
20. Renk, G., Grover, T., Crouch, R., Mao, B., and Ebrey, T. (1981) A spin labeled retinal pigment analogue of the purple membrane. Photochem. Photobiol. 33: 489–494.
21. Williams, T. C. and Mani, V. (1991) Design of a helix-bundle cross-link: NMR and UV-visible spectroscopic analysis and molecular modeling of ring-oxidized retinals. Biochemistry 30: 2976–2988.
22. Haag, A. and Eugster, C. H. (1980) Synthese von(−)-(R)-4-Hydroxy-β-ionon und(−)-(5S, 6S) -5-Hydroxy-4,5-dihydro-α-ionon aus(−)-S-α-Ionon. Helv. Chem. Acta 63: 10–15.
23. Haag, A. and Eugster, C. H. (1982) Isozeaxanthine: Chiralität und enantioselective Synthese von(4R, 4R') -Isozeaxanthin[(−)-(4R,4R')-β,β-Carotin-4,4'-diol]. Helv. Chim. Acta 65: 1795–1803.
24. Katsuta, Y., Yoshihara, K., Nakanishi, K., and Ito, M. (1994) Synthesis of (+)-(4S)- and (−)-(4R)-11Z-4-hydroxyretinals and determination of the absolute stereochemistry of a visual pigment chromophore in the bioluminescent squid, Watasenia scintillans, Tetrahedron Lett. 35: 905–908.
25. Kessler, J. F., Jones, S. E., Levine, N., Lynch, P. J., Booth, A. R., and Meyskens, F. L. (1987) Isotretinoin and cutaneous helper T-cell lymphoma (mycosis fungoides). Arch. Dermatol. 123: 201–204.
26. Clark, R., Jacobs, A., Lush, C., and Smith, S. A. (1987) Effect of 13-cis-RA on survival of patients with myelodysplastic syndrome. Lancet 1: 763–765.
27. Gudas, L. J., Sporn, M. B., and Roberts, A. B. (1994) Cellular biology and biochemistry of retinoids. In The Retinoids: Biology, Chemistry and Medicine. M. B. Sporn, A. B. Roberts, and D. S. Goodman, eds. Raven Press: New York, 443–520.
28. Vetter, W., Englert, N., Regassi, N., and Schweiter, U. (1971) Spectroscopic methods. In The Carotenoids. O. Isler, ed. Birkauser Verlag: Basel, 204–243.
29. Levin, A. A., Sturzenbecker, L. M., Kazmer, S. K., Bosakowski, T., Huselton, C., Allenby, G., Speck, J., Kratzeisen, C., Rosenberger, M., Lovey, A., and Grippo, J. F. (1992) 9-cis retinoic acid stereoisomer binds and activates the nuclear receptor RXRα. Nature 355:359–361.
30. Nervi, C., Grippo, J. R., Sherman, M. I., George, M. D, and Jetten, A. M. (1989) Identification and characterization of nuclear retinoic acid-binding activity inhuman 30. myeloblastic leukemia HL-60 cells. Proc. Natl. Acad. Sci. 86: 5854–5858.
31. Nervi, C., Poindexter, E. C., Grignani, F., Pandolfi, P. P., LoCoco, F., Avvisati, G., Pelicci, P. G., and Jetten, A. M. (1992) Characterization of the PML-RAR α chimeric product of the acute promyelocytic leukemia-specific 5 (15;17) translocation. Cancer Res. 52: 3687–3692.
32. Allenby, G., Bocquel, M-T., Saunders, M., Kazmer, S., Speck, J., Rosenberg, M., Lovey, A., Kastner, P., Grippo, J. F., Chambon, P., and Levin, A. A. (1993) Retinoic acid receptors and retinoid X receptors: interactions with endogenous retinoic acids. Proc. Natl. Acad. Sci. 90: 30–34.
33. Wagner, M., Han, B., and Jessell, T. M. (1992) Regional differences in retinoid release from embryonic neural tissue detected by an in vitro reporter assay. Development 116: 55–66.
34. LaRosa, G. J. and Gudas, L. J. (1988a) An early effect of retinoic acid cloning of an mRNA (ERA-1) exhibiting rapid and protein synthesis-independent induction during teratocarcinoma stem cell differentiation. Proc. Natl. Acad. Sci. 85: 329–333.
35. LaRosa, G. J., and Gudas, L. J. (1988b) Early retinoic acid induced F9 teratocarcinoma stem cell gene ERA-1: alternate splicing creates transcripts for a homeobox-containing protein and one lacking the homeobox. Mol. Cell. Biol. 8: 3906–3917.
36. Vasios, G. W., Gold, J. D., Petkovich, M., Chambon, P., and Gudas, L. J. (1989) A retinoic acid-responsive element is present in the 5' flanking region of the laminin B1 gene. Proc. Natl. Acad. Sci. 86: 9099–9103.
37. Williams, J. B. and Napoli, J. L. (1985) Metabolism of retinoic acid and retinol during differentiation of F9 embryonal carcinoma cells. Proc. Natl. Acad. Sci. 82: 4658–4662.
38. Boylan, J. F., and Gudas, L. J. (1992) The level of CRABP-I expression influences the levels and types of all-trans-retinoic acid metabolites in F9 teratocarcinoma stem cells. J. Biol. Chem. 267: 21486–21491.
39. Dawson, M. I., et al, Editors, Chemistry and Biology of Synthetic Retinoids, CRC Press Inc., 1990.

What is claimed is:

1. A method for treating deep acne in a patient afflicted with this condition comprising administering to said patient an acne clearing amount of a retinoid having the structure

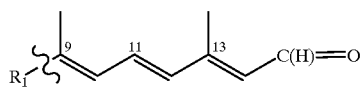

(I)

wherein the configuration at the 7-, 9-, 11- and 13-position double bonds is independently Z or E and wherein $R_1$ is selected from the group consisting of

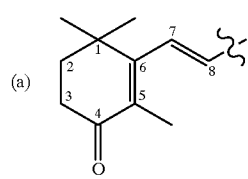

(I)

wherein the keto group at the 4-position is free or protected; and

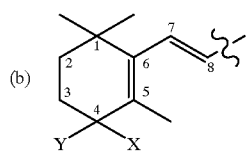

(II)

wherein X is selected from the group consisting of hydrogen and $C_{1-6}$-alkyl and wherein Y is selected from the group consisting of hydroxy and $C_{1-6}$-alkoxyl, and wherein the absolute configuration at the 4-position is independently R or S.

2. The method of claim 1 wherein the retinoid has the structure (II) where Y is methoxyl.

3. A method for treating deep acne in a patient afflicted with this condition comprising administering to said patient an acne clearing amount of a retinoid having the structure

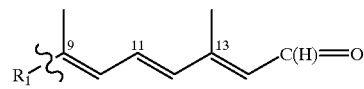

wherein the configuration at the 7-, 9-, 11- and 13-position double bonds is independently Z or E and wherein $R_1$ is selected from the group consisting of

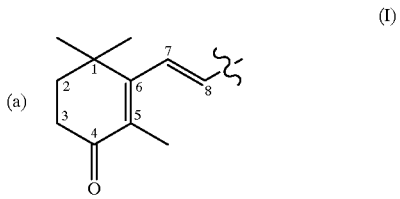

(I)

wherein the keto group at the 4-position is free or protected; and

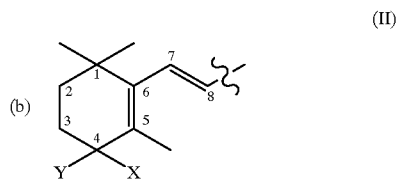

(II)

wherein X is selected from the group consisting of hydrogen and $C_{1-6}$-alkyl and wherein Y is hydroxyl.

4. The method of claim 3 where the retinoid is 4-oxo-retinaldehyde.

5. The method of claim 3 where the retinoid is 4-hydroxyretinaldehyde.

* * * * *

UNITED STATES PATENT AND TRADEMARK OFFICE
CERTIFICATE OF CORRECTION

PATENT NO. : 5,962,534
DATED : October 5, 1999
INVENTOR(S) : Lorraine J. Gudas et al.

It is certified that error appears in the above-identified patent and that said Letters Patent is hereby corrected as shown below:

Title page,
Delete what is opposite "[73]" and instead insert:

-- Assignees: Cornell Research Foundation, Inc., Ithaca; The Trustees of Columbia University in the City of New York, New York, both of N. Y. --

Signed and Sealed this

Fifth Day of February, 2002

Attest:

JAMES E. ROGAN
Attesting Officer
Director of the United States Patent and Trademark Office